(12) United States Patent
Asberom et al.

(10) Patent No.: US 6,683,091 B2
(45) Date of Patent: Jan. 27, 2004

(54) GAMMA SECRETASE INHIBITORS

(75) Inventors: Theodoros Asberom, West Orange, NJ (US); Henry S. Guzik, Brooklyn, NY (US); Hubert B. Josien, Hoboken, NJ (US); Dmitri A Pissarnitski, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/210,829

(22) Filed: Aug. 1, 2002

(65) Prior Publication Data

US 2003/0135044 A1 Jul. 17, 2003

Related U.S. Application Data

(60) Provisional application No. 60/355,510, filed on Feb. 6, 2002, and provisional application No. 60/310,013, filed on Aug. 3, 2001.

(51) Int. Cl.[7] ................ C07D 215/60; A61K 31/47
(52) U.S. Cl. ........................ 514/312; 546/153
(58) Field of Search ............... 514/312; 546/153

(56) References Cited

FOREIGN PATENT DOCUMENTS

| FR | 1328176 | * | 5/1963 |
| JP | 55006321 | * | 1/1980 |
| JP | 63095447 | * | 4/1988 |
| WO | WO 00/50391 | | 8/2000 |

OTHER PUBLICATIONS

Wang, CA 130:153558, abstract of Tetrahedron Letters, 39(52), 9605–9608, 1998.*

Iarock, CA 129:260327, abstract of Tetrahedron, 54(34), 9961–9980, 1998.*

Evans, CA 108:75203, abstract, 1987.*

Zhang, L., "*Biochemical Characterization of the γ–Secretase Activity . . .* ", Biochemistry, vol. 40, 2001, pp. 5049–5055.

Zhang, L., *Calpain Inhibitor I Increases B–Amyloid Peptide Production* , Journal of Biological Chemistry, vol. 274, No. 13, 1999, pp. 8966–8972.

* cited by examiner

*Primary Examiner*—D. Margaret Seaman
(74) *Attorney, Agent, or Firm*—Palaiyur S. Kalyanaraman; Henry C. Jeanette

(57) ABSTRACT

This invention discloses novel gamma secretase inhibitors of the formula:

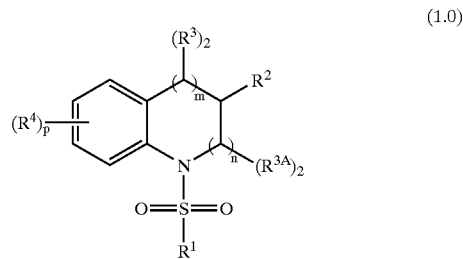

(1.0)

wherein: $R^1$ is a substituted aryl or substituted heteroaryl group; $R^2$ is an $R^1$ group, alkyl, $-X(CO)Y$, $-(CR^3_2)_{1-4}X(CO)Y$; each $R^{3A}$ is independently H or alkyl; X is $-O-$, $-NH$, or $-N$-alkyl; and Y is $-NR^6R^7$, or $-N(R^3)(CH_2)_{2-6}NR^6R^7$. Also disclosed is a method of treating Alzheimer's Disease.

15 Claims, No Drawings

GAMMA SECRETASE INHIBITORS

This patent application claims priority from provisional application Serial No. 60/310,013 filed Aug. 3, 2001, and provisional application Serial No. 60/355,510 filed Feb. 6, 2002.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

In view of the present interest in the treatment or prevention of neurodegenerative diseases, such as Alzheimer's disease, a welcome contribution to the art would be compounds for use in such treatment or prevention. This invention provides such a contribution.

SUMMARY OF THE INVENTION

This invention provides compounds that are inhibitors (e.g., antagonists) of Gamma Secretase and have the formula:

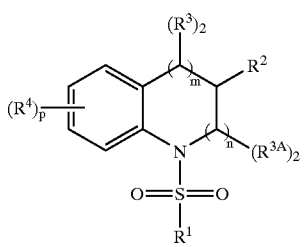

(1.0)

or a pharmaceutically acceptable salt or solvate thereof, wherein:

(A) $R^1$ is selected from:
  (1) unsubstituted aryl;
  (2) aryl substituted with one or more (e.g., 1–3) $R^5$ groups;
  (3) heteroaryl; or
  (4) heteroaryl substituted with one or more (e.g., 1–3) $R^5$ groups;

(B) $R^2$ is selected from:
  (1) alkyl;
  (2) —X(CO)Y;
  (3) —$(CR^3{}_2)_{1-4}$X(CO)Y; or
  (4) any of the groups for $R^1$;

(C) Each $R^3$ is independently selected from:
  (1) H, or
  (2) alkyl;

(D) Each $R^{3A}$ is independently selected from:
  (1) H; or
  (2) alkyl;

(E) $R^4$ is independently selected from:
  (1) halogen;
  (2) —$CF_3$;
  (3) —OH;
  (4) —Oalkyl;
  (5) —$OCF_3$;
  (6) —CN;
  (7) —$NH_2$;
  (8) —$CO_2$alkyl;
  (9) —$CONR^6R^7$;
  (10) -alkylene-$NR^6R^7$;
  (11) —$NR^6$COalkyl;
  (12) —$NR^6$COaryl;
  (13) —$NR^6$COheteroaryl; or
  (14) —$NR^6CONR^6R^7$;

(F) $R^5$ is independently selected from:
  (1) halogen;
  (2) —$CF_3$;
  (3) —OH;
  (4) —Oalkyl;
  (5) —$OCF_3$;
  (6) —CN;
  (7) —$NH_2$;
  (8) —$CO_2$alkyl;
  (9) —$CONR^6R^7$;
  (10) alkylene-$NR^6R^7$;
  (11) —$NR^6$COalkyl;
  (12) —$NR^6$COaryl;
  (13) —$NR^6$COheteroaryl;
  (14) —$NR^6CONR^6R^7$;

(G) X is selected from:
  (1) —O—;
  (2) —NH;
  (3) —N-alkyl; or (H) Y is selected from:
  (1) —$NR^6R^7$; or
  (2) —$N(R^3)(CH_2)_{2-6}NR^6R^7$;

(I) $R^6$ and $R^7$ are independently selected from:
  (1) H;
  (2) alkyl;
  (3) cycloalkyl;
  (4) -arylalkyl;
  (5) -heteroarylalkyl;
  (6)

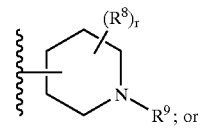

(a)

(7)

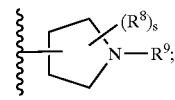

(b)

(J) $R^6$ and $R^7$ taken together with the nitrogen atom to which they are bound form a heterocycloalkyl group selected from:

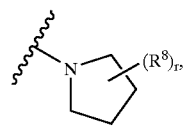

(c)

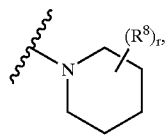

(d)

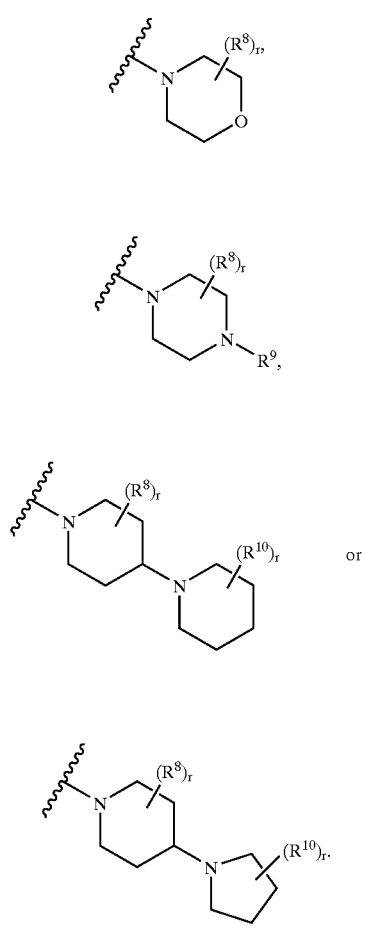

(K) Each $R^8$ is independently selected from:
  (1) alkyl; or
  (2) alkyl substituted with 1 to 4 hydroxy groups;
(L) Each $R^9$ is independently selected from:
  (1) H;
  (2) alkyl;
  (3) alkyl substituted with 1 to 4 hydroxy groups;
  (4) cycloalkyl;
  (5) cycloalkyl substituted with 1 to 4 hydroxy groups;
  (6) -arylalkyl;
  (7) -heteroarylalkyl;
  (8) —COOalkyl; or
  (9) any of the groups for $R^1$;
(M) Each $R^{10}$ is independently selected from:
  (1) H; or
  (2) alkyl;
(N) m is 0 to 3, and n is 0 to 3, such that m+n is 1, 2, 3 or 4;
(O) p is 0 to 4;
(P) r is 0 to 4;
(Q) s is 0 to 3; and
(R) with the proviso that compounds of formula 1.0 do not include:

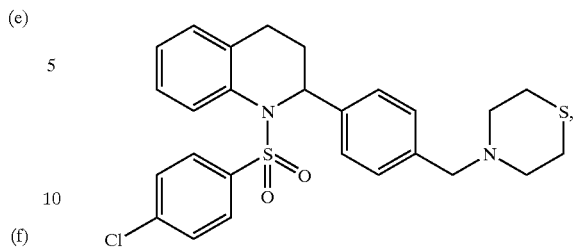

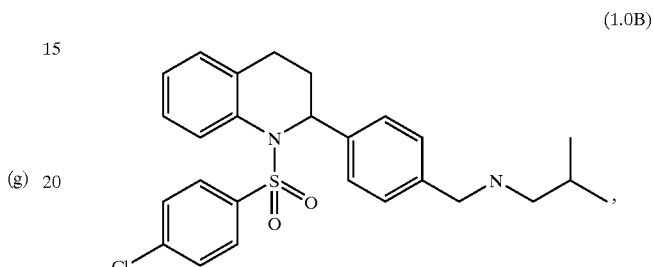

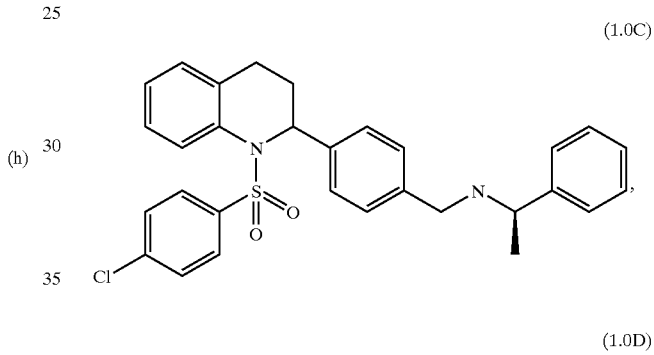

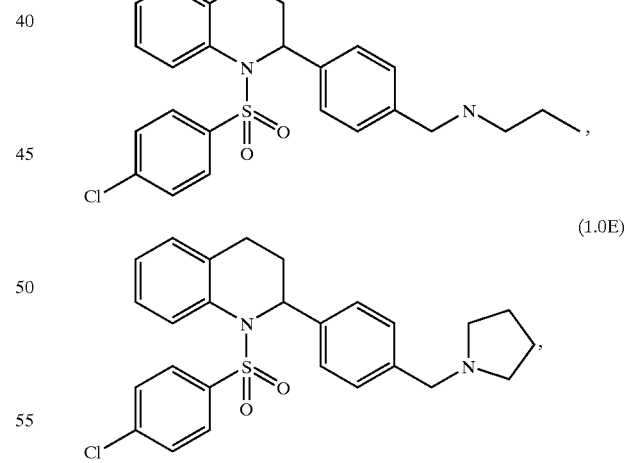

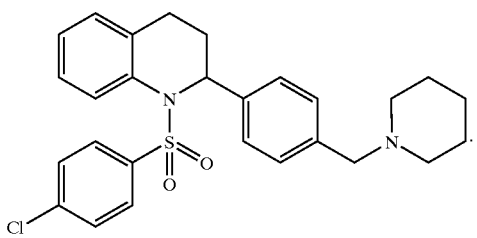
(1.0G)

This invention also provides a pharmaceutical composition comprising an effective amount of at least one compound of formula 1.0 and at least one pharmaceutically acceptable carrier.

This invention also provides a method for inhibiting gamma-secretase comprising administering an effective amount of a compound of formula 1.0 to a patient in need of treatment.

This invention also provides a method of treating neurodegenerative diseases comprising administering an effective amount of a compound of formula 1.0 to a patient in need of treatment.

This invention also provides a method of inhibiting the deposition of amyloid protein (e.g., amyloid β protein) in, on or around neurological tissue (e.g., the brain) comprising administering an effective amount of a compound of formula 1.0 to a patient in need of treatment.

This invention also provides a method of treating Alzheimer's disease comprising administering an effective amount of a compound of formula 1.0 to a patient in need of treatment.

DETAILED DESCRIPTION OF THE INVENTION

As used herein the following terms have the following meanings unless otherwise defined:

Patient includes both humans and other mammals. "Mammal" means, humans and other animals.

alkoxy: represents a —Oalkyl group wherein alkyl is as defined below;

alkyl: represents straight and branched carbon chains and contains from one to twenty carbon atoms, preferably one to six carbon atoms, said alkyl group being optionally substituted with one or more (e.g., 1, 2 or 3) substituents independently selected from: (1) halogen, (2) —OH, (3) —O(alkyl), preferably —O($C_1$–$C_6$) alkyl, and most preferably —$OCH_3$, (4) —$NH_2$, (5) —NH(alkyl), preferably —NH(($C_1$–$C_6$)alkyl), and most preferably —$NHCH_3$, (6) —N(alkyl)$_2$ wherein each alkyl group is independently selected, preferably —N(($C_1$–$C_6$)alkyl)$_2$ wherein each alkyl group is independently selected, and most preferably —N($CH_3$)$_2$ or (7) —S(alkyl), preferably —S(($C_1$–$C_6$)alkyl), and most preferably —$SCH_3$;

alkylene: represents a —(CH$_2$)$_q$— group wherein q is 1 to 20, generally 1 to 6 and more usually 1 to 4, optionally one or more (e.g., 1 to 3, or 1 to 2) hydrogens in said alkylene group can be replaced with the same or different alkyl group (preferably —($C_1$–$C_6$)alkyl, most preferably —($C_1$ to $C_3$)alkyl, more preferably —($C_1$–$C_2$)alkyl) such that the total number of carbons in the entire alkylene group is 2 to 20, also said alkylene group can be optionally substituted with one or more (e.g., 1 to 3) substituents independently selected from the group consisting of: (1) halo; (2) —OH; (3) —O(alkyl), preferably —O(($C_1$–$C_6$)alkyl), and most preferably —$OCH_3$; (4) —$NH_2$; (5) —NH(alkyl), preferably —NH(($C_1$–$C_6$)alkyl), and most preferably —$NHCH_3$; (6) —N(alkyl)$_2$ wherein each alkyl group is independently selected, preferably —N(($C_1$–$C_6$)alkyl)$_2$ wherein each alkyl group is independently selected, and most preferably —N($CH_3$)$_2$; and (7) —S(alkyl), preferably —S(($C_1$–$C_6$)alkyl), and most preferably —$SCH_3$;

ar: represents aryl as defined below;

aralkyl (arylalkyl): represents an aryl group, as defined below, bound to an alkyl group, as defined above, wherein said alkyl group is bound to a molecule (e.g., a compound of the claimed invention or an intermediate to a compound of the invention);

aryl: represents a carbocyclic group containing from 6 to 15 carbon atoms and having at least one aromatic ring (e.g., phenyl, naphthyl, phenanthryl, tetrahydronaphthyl or indanyl), with all available substitutable carbon atoms of the carbocyclic group being intended as possible points of attachment; said carbocyclic group being optionally substituted with one or more (e.g., 1 to 3) substituents independently selected from: (1) halo, (2) alkyl (preferably —($C_1$ to $C_6$)alkyl), (3) hydroxy, (4) alkoxy (preferably —(C, to $C_6$)alkoxy), (5) —CN, (6) —$CF_3$, (7) amino (—$NH_2$), (8) alkylamino, (9) dialkylamino (wherein each alkyl group is independently selected), (10) aryl (e.g., phenyl) (provided that if this aryl group is optionally substituted with one or more aryl groups these latter aryl groups are not further substituted with aryl groups), (11) aralkoxy (provided that if the aryl moiety of said aralkoxy (i.e., arylalkoxy) group is optionally substituted with one or more aryl groups these latter aryl groups are not further substituted with aryl groups), (12) aryloxy (e.g., phenoxy) (provided that if the aryl moiety of said aryloxy group is optionally substituted with one or more aryl groups these latter aryl groups are not further substituted with aryl groups), (13) —S(O)$_{0-2}$-aryl (provided that if the aryl moiety of said —S(O)$_{0-2}$-aryl group is optionally substituted with one or more aryl groups these latter aryl groups are not further substituted with aryl groups), (14) —COOR$^{11}$ or (15) —NO$_2$; wherein said R$^{11}$ represents H, alkyl, aryl (provided that if said aryl moiety is optionally substituted with one or more aryl containing groups these latter aryl containing groups are not further substituted with aryl containing groups), or aralkyl (e.g., benzyl) (provided that if said aryl moiety of said aralkyl group is optionally substituted with one or more aryl containing groups these latter aryl containing groups are not further substituted with aryl containing groups); preferably said optional substituents are independently selected from: halogen, —$CF_3$, —($C_1$ to $C_6$)alkyl, —($C_1$ to $C_6$)alkoxy, —$OCF_3$, —$NH_2$, or —CN;

cycloalkyl: represents a cyclic alkyl group of 3 to 10 carbon atoms, and usually 3 to 8 carbon atoms, said cycloalkyl group being optionally substituted with one or more (e.g., 1, 2 or 3) substituents independently selected from:(1) halogen, (2)—OH, (3) —O(alkyl), preferably —O($C_1$–$C_6$)alkyl, and most preferably —$OCH_3$, (4) —$NH_2$, (5) —NH(alkyl), preferably —NH(($C_1$–$C_6$)alkyl), and most preferably —$NHCH_3$, (6) —N(alkyl)$_2$ wherein each alkyl group is independently selected, preferably —N(($C_1$–$C_6$)alkyl)$_2$ wherein each alkyl group is independently selected, and most preferably —N(CH$_3$)$_2$, (7) —S(alkyl), preferably —S((C$_1$–C$_6$)alkyl), and most preferably —SCH$_3$, or (8) alkyl, preferably —(C$_1$–C$_6$)alkyl;

halogen (halo): represents fluoro, chloro, bromo and iodo;

heteroaryl: represents a monocyclic, bicyclic or tricyclic group having at least one heteroatom (e.g., 1, 2 or 3) independently selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, imidazolyl, thienyl, furanyl, quinolyl, isoquinolyl, benzofuranyl, benzopyranyl, benzothienyl, thiazolyl, indolyl, naphthyridinyl, pyridyl (e.g., 2-, 3- or 4-pyridyl) or pyridyl N-oxide (e.g., 2-, 3- or 4-pyridyl N-oxide), wherein pyridyl N-oxide can be represented as:

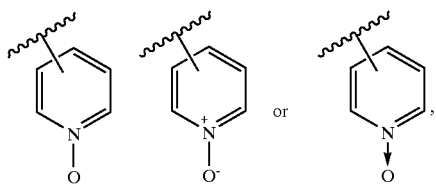

and with all available substitutable carbon and heteroatoms of the cyclic group being intended as possible points of attachment, said cyclic group being optionally substituted with one or more (e.g., 1, 2 or 3) groups independently selected from: (1) halo, (2) alkyl (preferably —(C$_1$ to C$_6$)alkyl), (3) aryl, (4) aralkyl, (5) hydroxy, (6) alkoxy (preferably —(C$_1$ to C$_6$)alkoxy), (7) phenoxy, (8) —NO$_2$, (9) —CF$_3$, (10) —OCF$_3$, (11) —CN, (12) amino (—NH$_2$), (13) alkylamino, (14) dialkylamino (wherein each alkyl is independently selected), (15) —COOR$^{11}$ (wherein R$^{11}$ is as defined above), or

(16) heteroaryl (provided that if this heteroaryl group, as defined above, is optionally substituted with one or more heteroaryl groups these latter heteroaryl groups are not further substituted with heteroaryl groups); preferably said optional substituents are independently selected from: halogen, —CF$_3$, —(C$_1$ to C$_6$)alkyl, —(C$_1$ to C$_6$)alkoxy, —OCF$_3$, —NH$_2$, or —CN;

heteroaralkyl (heteroarylalkyl): represents a heteroaryl group, as defined above, bound to an alkyl group, as defined above, wherein said alkyl group is bound to a molecule (e.g., a compound of the claimed invention or an intermediate to a compound of the invention);

heterocycloalkyl: represents a cycloalkyl ring as defined above, having one or more (e.g., 1, 2 or 3) heteroatoms independently selected from: O, S, or —NR$^{12}$— wherein R$^{12}$ is selected from: H, alkyl, aryl, heteroaryl, ar(C$_1$ to C$_6$)alkyl, or heteroar(C$_1$ to C$_6$)alkyl;

TFA: represents trifluroacetic acid; and

THF: represents tetrahydrofuran.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. For example, "one or more" or "at least one" can mean 1 to 6 moieties, and generally 1 to 4 moieties, and usually 1 to 3 moieties.

The term "effective amount" as used in the methods and pharmaceutical compositions of this invention means a therapeutically effective amount and is meant to describe an amount of a compound of the present invention to treat a patient having a disease or condition intended to be treated and thus produce a desired therapeutic effect.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems indicate that the indicated bond may be attached to any of the substitutable ring carbon atoms.

Certain compounds of the invention may exist in different isomeric (e.g., enantiomers and diastereoisomers) forms. The invention contemplates all such isomers both in pure form and in admixture, including racemic mixtures. Enol forms are also included.

The compounds of the invention can be administered as racemic mixtures or enantiomerically pure compounds.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Preferably:

R$^1$ is aryl substituted with one or more R$^5$ groups, most preferably phenyl substituted with one or more R$^5$ groups, and more preferably phenyl substituted with one or more halo atoms;

n is 0 or 1 and m is 1 or 2 such that m+n is 2 (i.e., (i) n is 0 and m is 2, or (ii) n is 1 and m is 1), most preferably n is 0 and m is 2;

p is 0 or 1, and when p is 1 $R^4$ is halo; and
$R^2$ is —X(CO)Y or —$(CR^3_2)_{1-4}$X(CO)Y.

Most preferably:

$R^1$ is aryl substituted with one or more $R^5$ groups, more preferably phenyl substituted with one or more $R^5$ groups, and even more preferably phenyl substituted with one or more halo atoms;

n is 0 or 1 and m is 1 or 2 such that m+n is 2 (i.e., (i) n is 0 and m is 2, or (ii) n is 1 and m is 1), most preferably n is 0 and m is 2;

p is 0 or 1, and when p is 1 $R^4$ is halo;

$R^2$ is —X(CO)Y or —$(CR^3_2)_{1-4}$X(CO)Y;

X is —O—; and

Y is —$NR^6R^7$.

More preferably:

$R^1$ is aryl substituted with one or more $R^5$ groups, even more preferably phenyl substituted with one or more $R^5$ groups, and still even more preferably phenyl substituted with one or more halo atoms;

n is 0 or 1 and m is 1 or 2 such that m+n is 2 (i.e., (i) n is 0 and m is 2, or (ii) n is 1 and m is 1), most preferably n is 0 and m is 2;

p is 0 or 1, and when p is 1 $R^4$ is halo;

$R^2$ is —X(CO)Y or —$(CR^3_2)_{1-4}$X(CO)Y;

X is —O—;

Y is —$NR^6R^7$; and $R^6$ and $R^7$ are independently selected from: H, methyl, ethyl —$(C_3-C_8)$cycloalkyl, -aryl$(C_1-C_6)$alkyl, 4-pyridylmethyl,

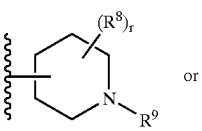
(a)

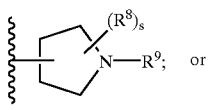
(b)

$R^6$ and $R^7$ taken together with the nitrogen atom to which they are bound form a heterocycloalkyl group selected from:

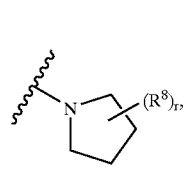
(c)

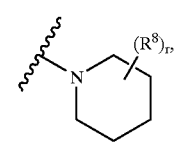
(d)

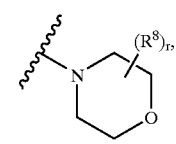
(e)

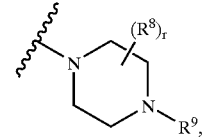
(f)

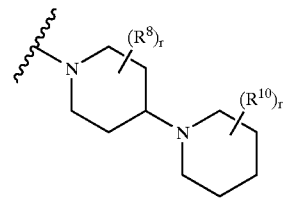
(g)

or

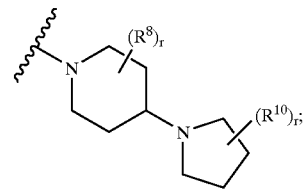
(h)

Preferably

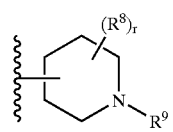
(a)

is a group of the formula:

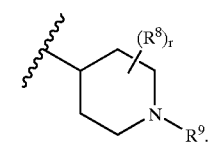
(a1)

Preferably

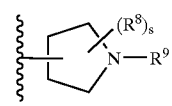
(b)

is a group of the formula:

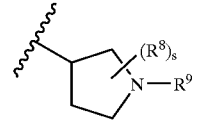
(b1)

Representative compounds of the invention include but are not limited to the compounds of Examples 1 to 100. Preferred compounds of the invention are the compounds of Examples 35, 39, 41, 43, 56, 58, 59, 61, 70, 70A, 77, 78, 98, 99 and 100.

Compounds of formula 1.0 can be prepared by various methods well known to those skilled in the art. For example, compounds of formula 1.0, wherein $R^2$ is —X(CO)Y or —$(CH_2)_{1-4}$X(CO)Y (hereinafter represented as —$(CH_2)_{0-4}$X(CO)Y), and X and Y are as previously defined above, can be prepared as shown in Scheme 1.

Scheme 1

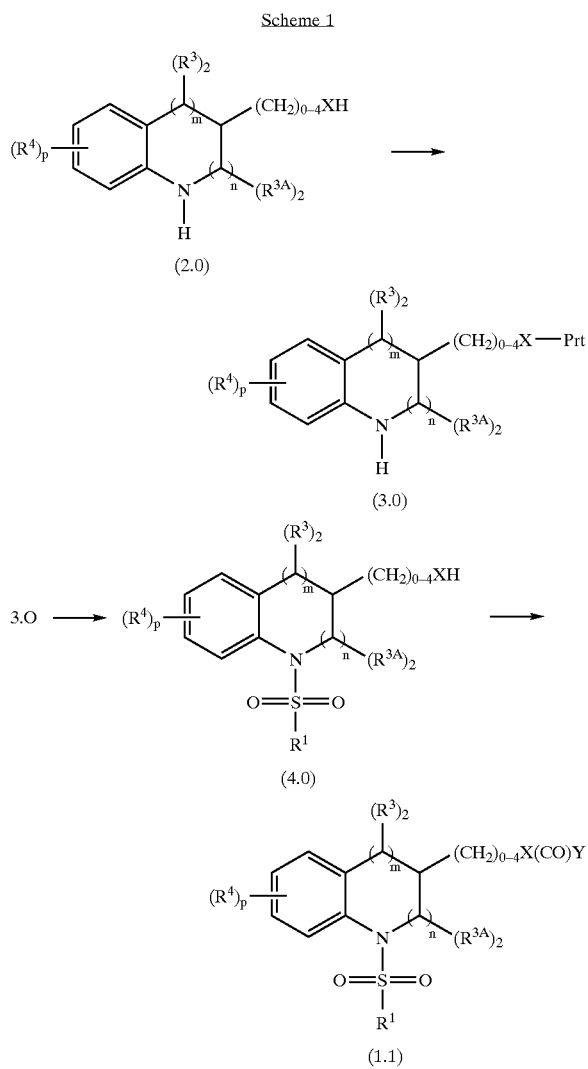

Precursor amines or alcohols 2.0 are protected with a suitable protecting group "Prt" to give protected derivative 3.0. Protecting groups for alcohols and amines are well known to those skilled in the art, and include trialkylsilyl groups, alkyl and arylcarbamates, amides, and esters. The protected derivative 3.0 is then treated with a sulfonyl halide $R^1SO_2Hal$ (where Hal=a halogen) in the presence of a suitable base such as triethylamine or sodium hydride, to give sulfonamide 4.0. The protecting group is removed under appropriate conditions known to those skilled in the art, such as methanolic or aqueous base (e.g., sodium hydroxide or potassium carbonate), aqueous or methanolic acid (e.g., hydrochloric acid) or tetra-n-butylammonium fluoride. This is then converted to various esters, amides, carbamates, and carbonates using methods well known to those skilled in the art. These methods include reaction with an appropriate carboxylic acid chloride, reaction with a carboxylic acid in the presence of an activating agent such as dicyclohexylcarbodiimide or hydroxybenzotriazole, reaction with an alkyl or arylchloroformate, reaction with an arylchloroformate followed by reaction with an amine or alcohol. Compounds of 2.0 are either commercially available or can be prepared by methods well known in the art as are described in the examples below.

Compounds of formula 1.0 wherein $R^2$ is aryl substituted with one or more $R^5$ groups can be, for example, prepared as described in Scheme 2.

Scheme 2

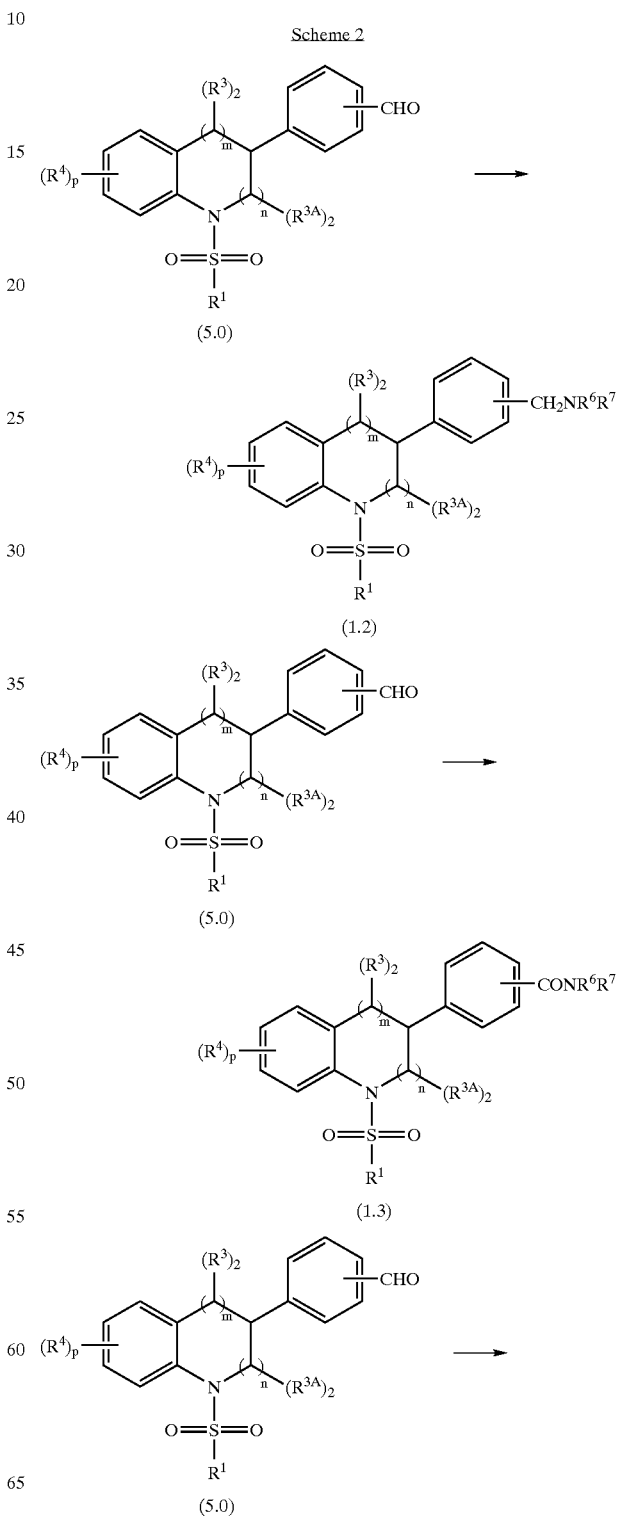

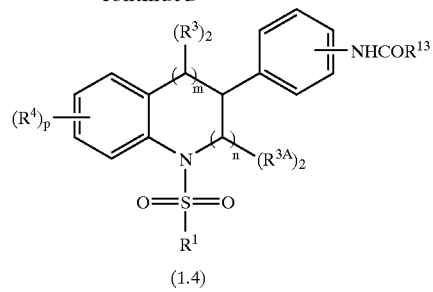

(1.4)

$R^{13}$ represents alkyl, aryl or —$NR^6R^7$. Aldehyde 5.0 is converted to a variety of substituted compounds via methods well known to those skilled in the art. For example, 5.0 can be treated with a primary or secondary amine in the presence of a reducing agent such as triacetoxyborohydride and in a suitable solvent such as dichloroethane to give an aminoalkyl derivative 1.2. Aldehyde 5.0 can be oxidized to the corresponding carboxylic acid with, for instance, Jones reagent, and then converted to amides (1.3). Alternatively, the acid can be converted to an amine with diphenylphosphorylazide and the amine converted to amides or ureas (1.4). Aldehyde 5.0 can be prepared by methods known in the art and by the methods described in the examples below.

Compounds of this invention are exemplified by the following examples, which should not be construed as limiting the scope of the disclosure. Alternative mechanistic pathways and analogous structures within the scope of the invention may be apparent to those skilled in the art.

In the following examples, "HRMS(MH⁺)" refers to the measured high resolution mass of the compound. "LCMS (MH⁺); Rt (min)" refers to the mass and retention time as determined by LC-Mass spectrum carried out on an Alltech Platinum C8 column (33 mm×7 mm ID, 3 micron particle size). Elution conditions for LC/MS are as follows: Solvents: A. Water w/0.05% TFA (v/v); B. Acetonitrile w/0.05% TFA (v/v); Flow Rate: [31]1 mL/min

| Gradient Method: | |
|---|---|
| Time (min) | % B Conc |
| 0 | 10 |
| 5 | 95 |
| 7 | 95 |
| 7.5 | 10 |
| 9 | STOP |

EXAMPLE 1

Preparation of (3-Imidazol-1-yl-propyl)-carbamic Acid 1-(4-chloro-benzenesulfonyl)-1,2,3,4-tetrahydro-quinolin-2-yl methyl Ester Step 1:

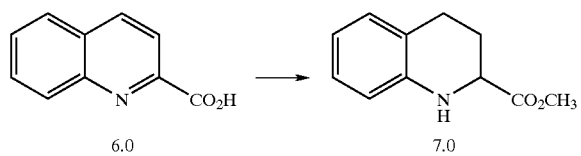

Quinaldic acid 6.0 (2.0 g, 11.6 mmol) in methanol (15 mL) was hydrogenated over platinum oxide (60 mg) under an atmospheric pressure of hydrogen at ambient temperature until the theoretical amount of hydrogen was consumed. The mixture was filtered through Celite, and to the filtrate was added dropwise, thionyl chloride (1.3 mL, 18 mmol) at 0° C. The mixture was stirred overnight at ambient temperature and concentrated at reduced pressure. The residue was dissolved in water and neutralized with saturated aqueous sodium bicarbonate. The mixture was extracted with ethyl acetate, and the organic layer was washed with brine, dried over magnesium sulfate, and concentrated. The crude residue was purified by silica gel chromatography eluting with 15% ethyl acetate:hexane to give the title compound (1.1 g, yield 50%) as a pale yellow oil: $^1$H NMR (300 MHz, CDCl$_3$)δ 7.02 (dd, 2H, J=8.7 Hz), 6.67 (dt, 2H, J=7.5 Hz), 4.40 (br, 1H), 4.06 (dd, 1H, J=3.6, 3.9 Hz), 3.80 (s, 3H), 2.24–2.36 (m, 1H), 1.95–2.10 (m, 1H).

Step 2:

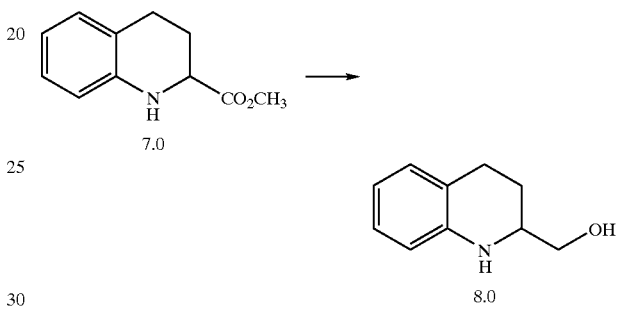

To a solution of LiAlH$_4$ (34 mL, 1M THF) was added dropwise 2-(methoxycarbonyl)tetrahydroquinoline 7.0 (3.19 g, 16.7 mmol) in THF (30 mL) at room temperature. The mixture was refluxed for 3.5 h, and the excess reagent was decomposed by addition of aqueous THF. To the mixture was added 1 N aqueous NaOH (14 mL), water (28 mL), and diethyl ether (28 mL), successively. The organic layer was separated, washed with brine, dried over magnesium sulfate, and concentrated. The residue was purified by silica gel chromatography with 1:1 ethyl acetate/hexane to give the title compound (2.29 g, yield 85%) as pale yellow oil: LC-MS (ESI) m/e 164 (M+1)⁺.

Step 3:

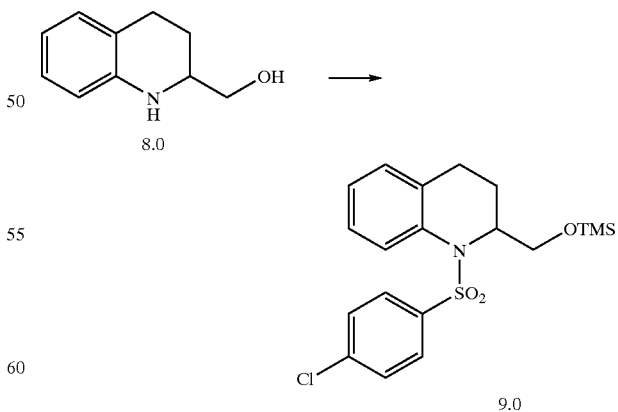

To a solution of 2-(hydroxymethyl)tetrahydroquinoline 8.0 (1.57 g, 9.63 mmol) in dichloroethane (24 mL) containing triethylamine (2.2 mL, 15.75 mmol) was added trimethylsilyl chloride (1.4 mL, 11.19 mmol) at 0° C. The mixture was stirred for 30 min at 0° C. followed by addition of triethylamine (2.2 mL) and p-chlorobenzenesulfonyl chloride (2.2 g, 10.43 mmol). The mixture was stirred at reflux for 16 h, and water was added. The organic layer was separated, washed with water, dried over magnesium sulfate, and concentrated. The residue was purified by silica gel chromatography with 3:7 hexane/ethyl acetate to give the title compound (1.81 g, yield 46%) as pale yellow oil: $^1$H NMR (300 MHz, CDCl$_3$) δ 7.52 (d, 1H, J=4.7 Hz), 7.37 (dd, 4H, J=5.1, 7.2 Hz), 7.24 (t, 1H, J=7.2 Hz), 7.15 (t, 1H, J=1.2 Hz), 6.96 (d, 1H, J=6.9 Hz), 4.10–4.26 (m, 1H), 1.95–2.06 (m, 1H), 1.49–1.62 (m, 2H), 0.10 (s, 9H).

Step 4:

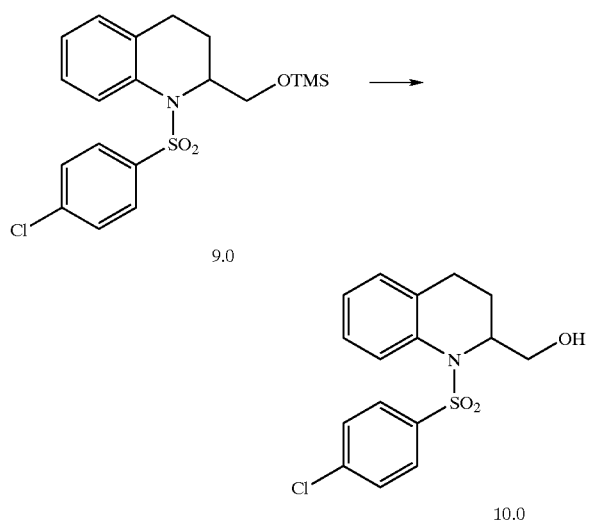

To a solution of 9.0 (1.62 g, 3.96 mmol) in anhydrous methanol (10 mL) was added solid potassium carbonate (4 mg, 0.03 mmol). The mixture was stirred for 45 min at 0° C., and then acidified with glacial acetic acid. The mixture was extracted with ethyl acetate, dried over magnesium sulfate, and concentrated. The residue was purified by silica gel chromatography with 1:3 ethyl acetate/hexane to give the title compound (1.20 g, yield 90%) as yellow viscous oil: LC-MS (ESI) m/e 338 (M+1)$^+$.

The two enantiomers of 10.0 were separated by preparative HPLC. The following conditions were used for the AS chiralpack column: hexane/isopropanol, 90/10, 45 ml/min, 254 nm, 117.41 min (isomer A), 256.51 min (isomer B). From 600 mg of 10.0, 258 mg of isomer A and 230 mg of isomer B were obtained. Each enantiomer was independently converted to the enatiomerically pure carbamates 12.0, according to the following steps 5 and 6.

Isomer A: [α]D=−209.88°(c=5.13 mg/ml, CH$_3$Cl)

Isomer B: [α]D=+186.31°(c=5.01 mg/ml, CH$_3$Cl).

Step 5:

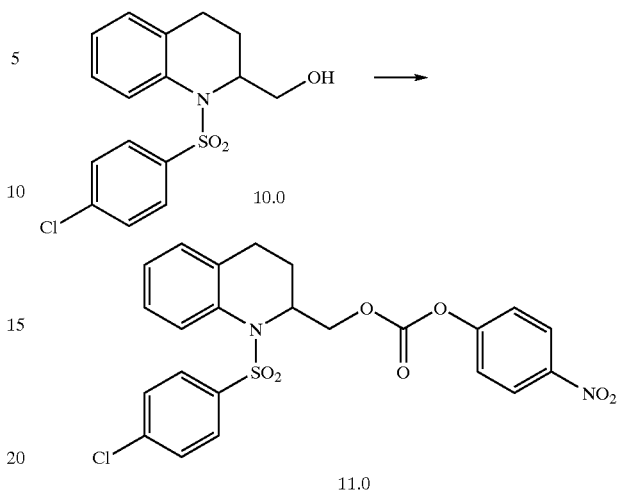

To a solution of 10.0 (204 mg, 0.6 mmol) in THF (6 mL) and acetonitrile (6 mL) was added pyridine (51 mg, 0.65 mmol) followed by 4-nitrophenyl chloroformate (133 mg, 0.66 mmol). The resulting mixture was allowed to stir at 22° C. for 16 h. The solvents were removed at reduced pressure, and the product was dissolved in ether, washed with water, the brine. The ether layer was dried over magnesium sulfate, filtered, and concentrated. Silica gel chromatography (ethyl acetate:hexane, 20%) of the concentrate gave the title compound (243 mg, yield 80%) as a colorless oil: LC-MS (ESI) m/e 504 (M+1)$^+$, 328.

Step 6:

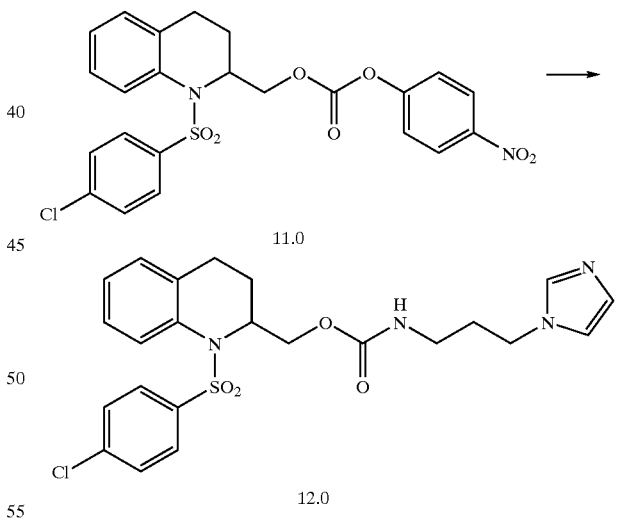

To a solution of the above carbonate 11.0 (25 mg, 0.05 mmol) in methanol (0.5 ml) was added 3-aminopropyl-(1 H)-imidazole (14 mg, 0.11 mmol). The resulting mixture was allowed to stir at 22° C. for 16 h, then concentrated at reduced pressure. Silica gel chromatography (methanol in CH$_2$CL$_2$, 5%) of the concentrate afforded the title compound (10.9 mg, yield 45%) as a pale yellow viscous oil: LC-MS (ESI) m/e 490 (M+1)$^+$, 320.

Following procedures similar to those of Example 1, the carbamates in Table 1 were prepared. In Table 1, "Ex." represents "Example".

TABLE 1

| Ex. | Structure | LC-MS (ESI) m/e |
|---|---|---|
| 2 | 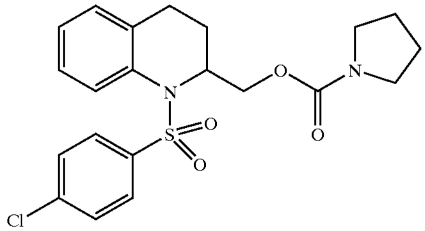 | 435(M + 1)+, 320, 260 |
| 3 | 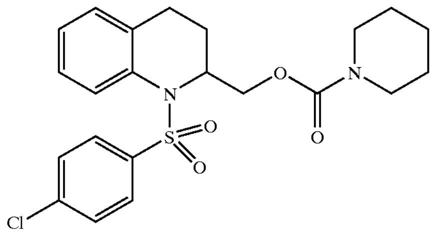 | 450(M + 1)+, 320 |
| 4 | 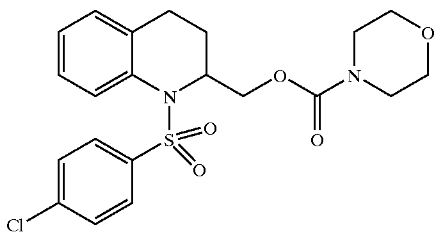 | 452(M + 1)+, 276 |
| 5 | 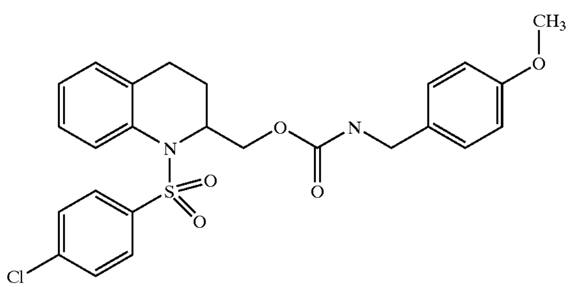 | 502(M + 1)+ |
| 6 | 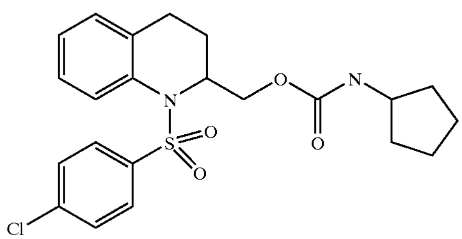 | 450(M + 1)+, 338, 247 |
| 7 | 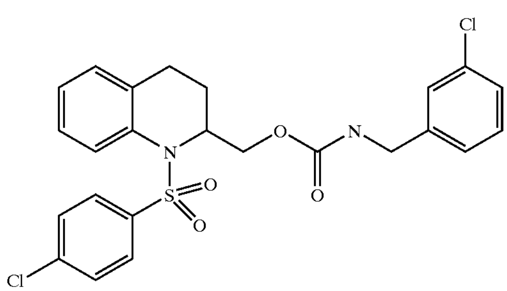 | 506(M + 1)+, 330 |

TABLE 1-continued
| Ex. | Structure | LC-MS (ESI) m/e |
|---|---|---|
| 8 | 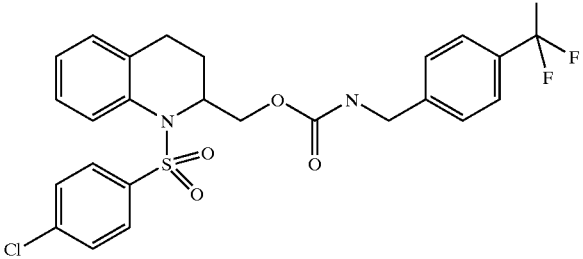 | 540(M + 1)+, 364 |
| 9 | 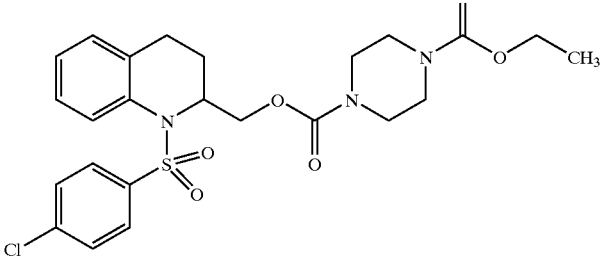 | 523(M + 1)+, 347 |
| 10 | 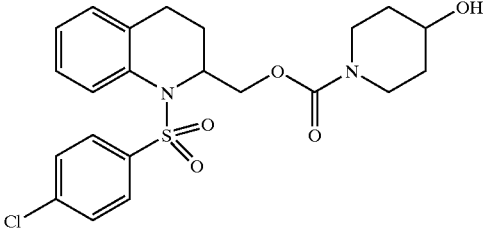 | 466(M + 1)+, 320, 290 |
| 11 | 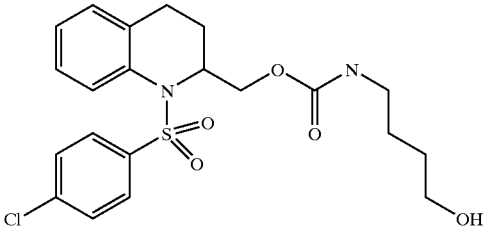 | 454(M + 1)+, 338, 320 |
| 12 | 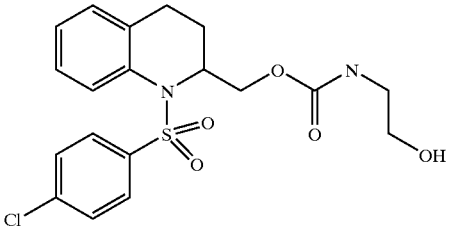 | 426(M + 1)+, 320, 250 |
| 13 | 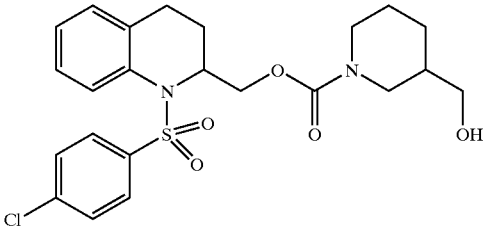 | 480(M + 1)+, 320, 304 |

TABLE 1-continued
| Ex. | Structure | LC-MS (ESI) m/e |
|---|---|---|
| 14 | 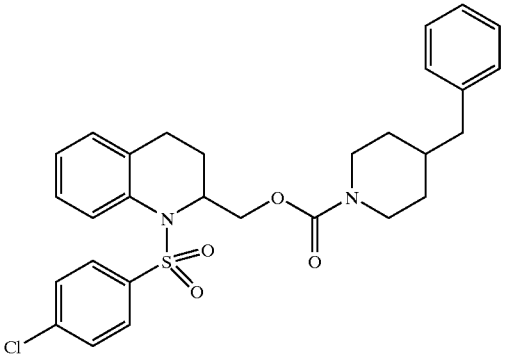 | 540(M + 1)+, 364, 320 |
| 15 | 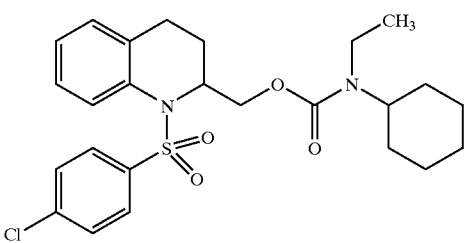 | 492(M + 1)+, 322, 320 |
| 16 | 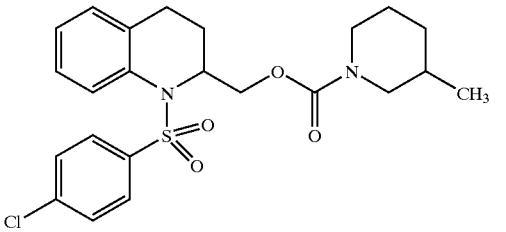 | 464(M + 1)+, 320, 288 |
| 17 | 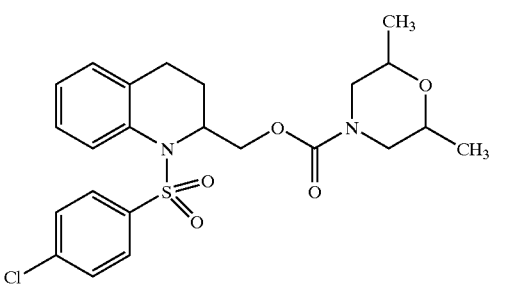 | 480(M + 1)+, 320, 304 |
| 18 | 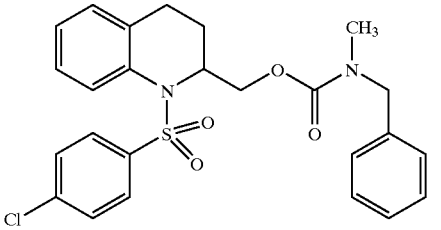 | 486(M + 1)+, 320, 310 |

TABLE 1-continued

| Ex. | Structure | LC-MS (ESI) m/e |
|---|---|---|
| 19 | 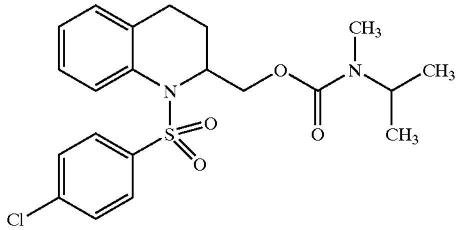 | 438(M + 1)+, 320, 262 |
| 20 | 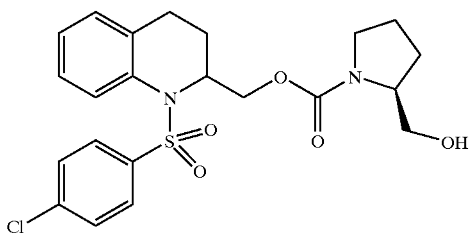 | 466(M + 1)+, 320 |
| 21 | 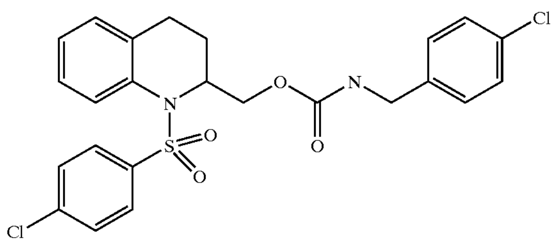 | 506(M + 1)+, 338, 330, 320 |
| 22 | 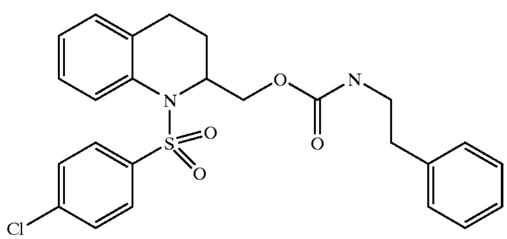 | 486(M + 1)+, 338, 320, 310 |
| 23 | 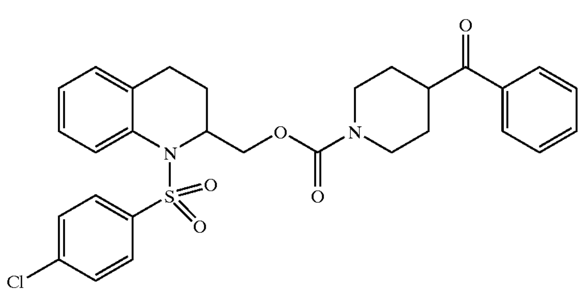 | 554(M + 1)+, 378, 320 |
| 24 | 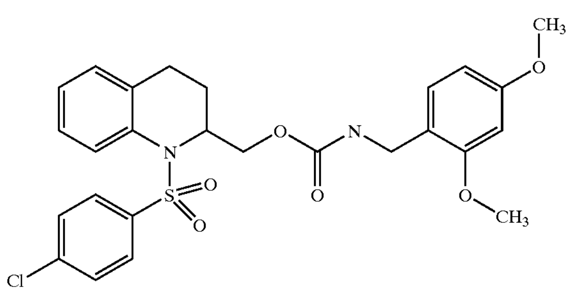 | 532(M + 1)+, 301 |

TABLE 1-continued
| Ex. | Structure | LC-MS (ESI) m/e |
|---|---|---|
| 25 | 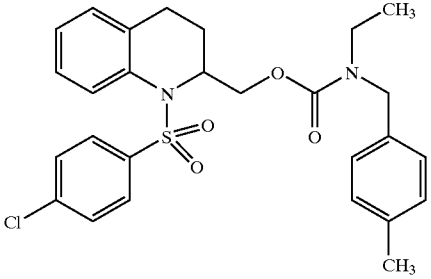 | 514(M + 1)+, 338, 320 |
| 26 | 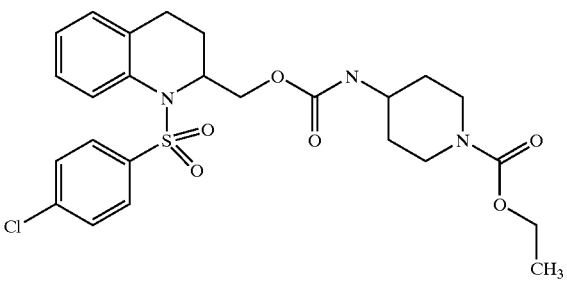 | 537(M + 1)+, 361, 338, 320 |
| 27 | 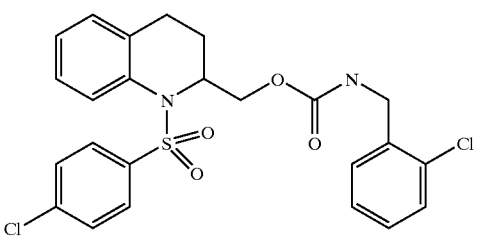 | 506(M + 1)+, 338, 330, 320 |
| 28 | 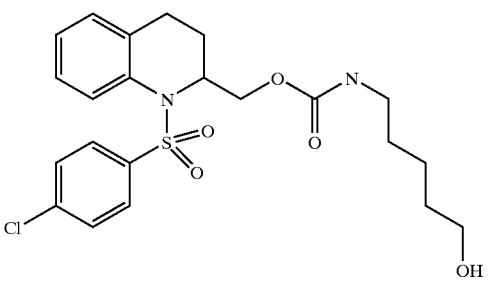 | 468(M + 1)+, 338, 320, 292 |
| 29 | 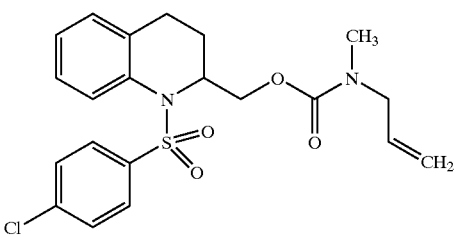 | 436(M + 1)+, 320, 260 |

TABLE 1-continued

| Ex. | Structure | LC-MS (ESI) m/e |
|---|---|---|
| 30 | 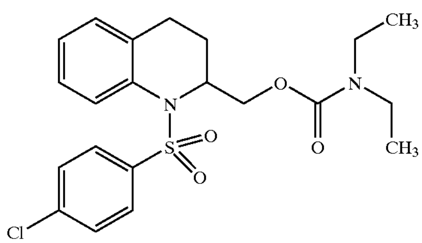 | 438(M + 1)+, 320, 262 |
| 31 | 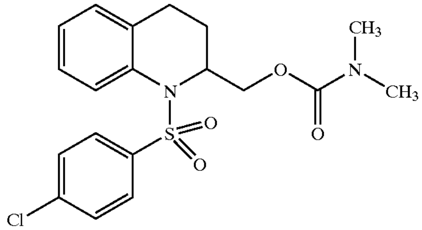 | 410(M + 1)+, 320, 234 |
| 32 | 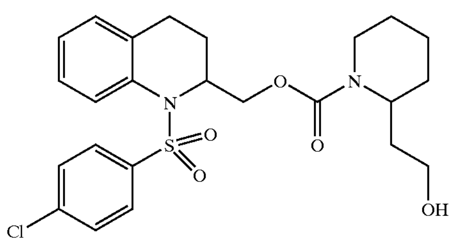 | 494(M + 1)+ |
| 33 | 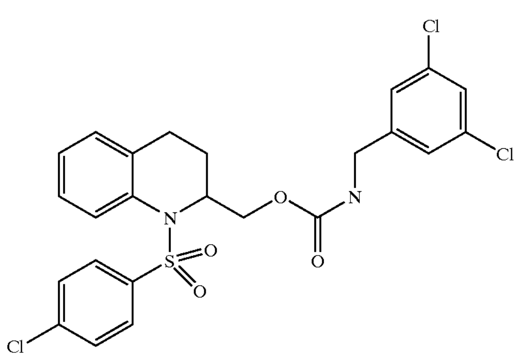 | 542(M + 1)+ |
| 34 | 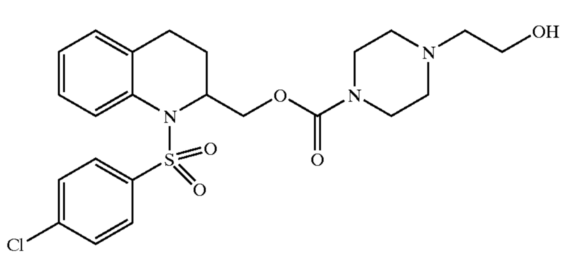 | 495(M + 1)+ |

TABLE 1-continued
| Ex. | Structure | LC-MS (ESI) m/e |
|---|---|---|
| 35 | 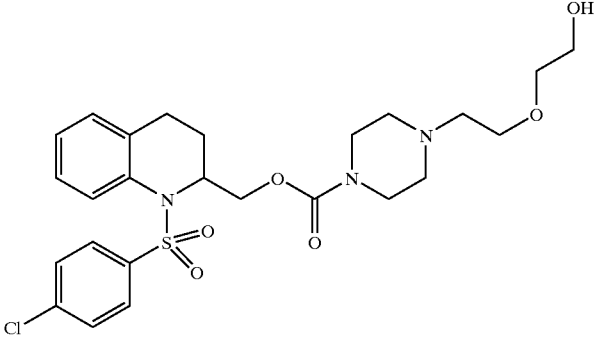 | 539(M + 1)+ |
| 36 | 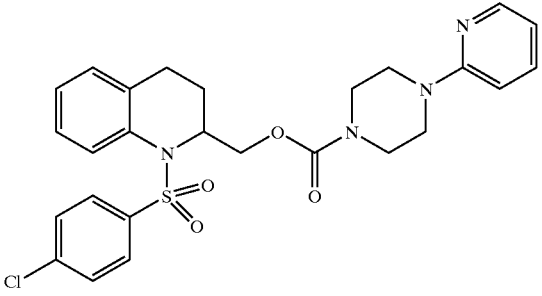 | 528(M + 1)+ |
| 37 | 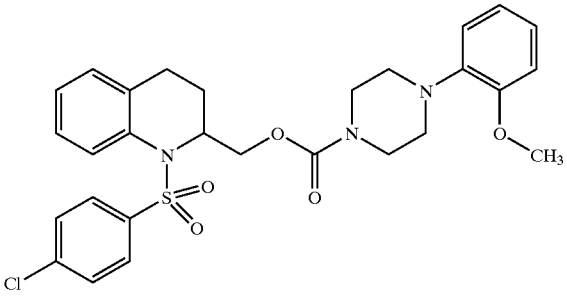 | 557(M + 1)+ |
| 38 | 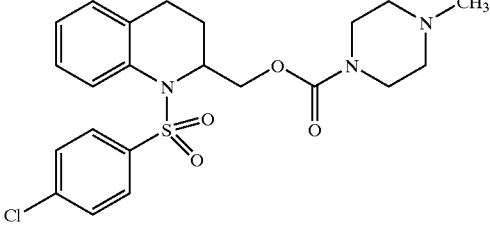 | 465(M + 1)+ |
| 39 | 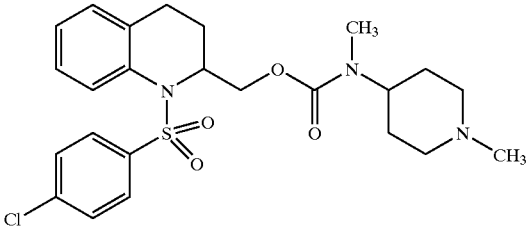 | 493(M + 1)+ |

TABLE 1-continued

| Ex. | Structure | LC-MS (ESI) m/e |
|---|---|---|
| 40 | 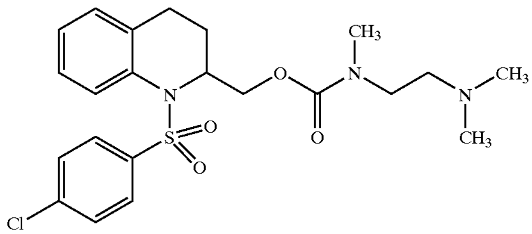 | 467(M + 1)+ |
| 41 | 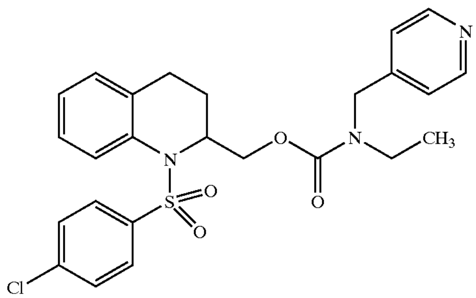 | 501(M + 1)+ |
| 42 | 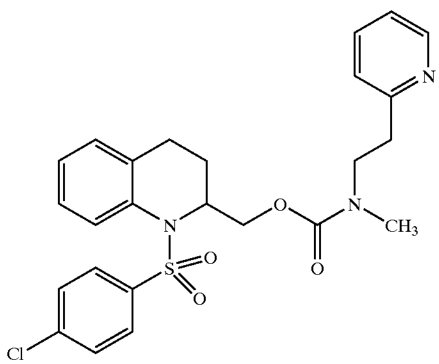 | 501(M + 1)+ |
| 43 | 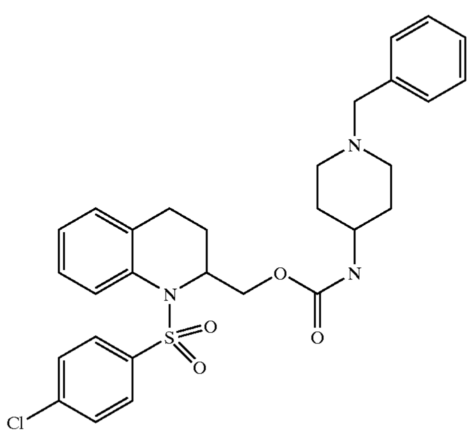 | 555(M + 1)+ |

TABLE 1-continued
| Ex. | Structure | LC-MS (ESI) m/e |
|---|---|---|
| 44 | 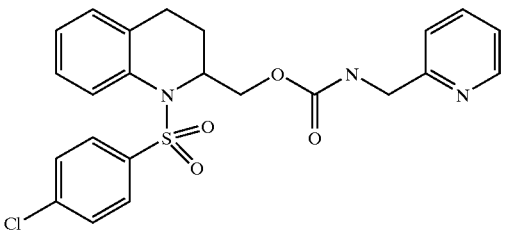 | 473(M + 1)+ |
| 45 | 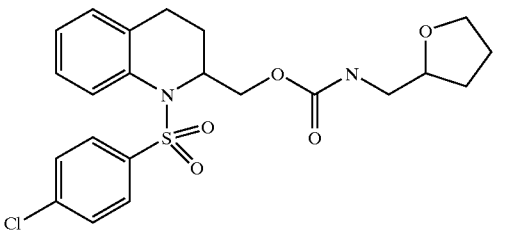 | 466(M + 1)+ |
| 46 | 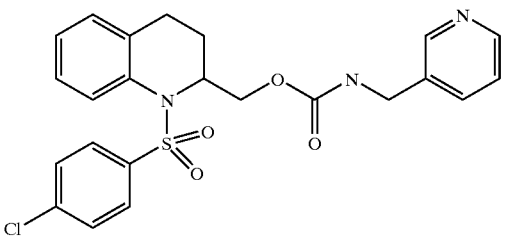 | 473(M + 1)+ |
| 47 | 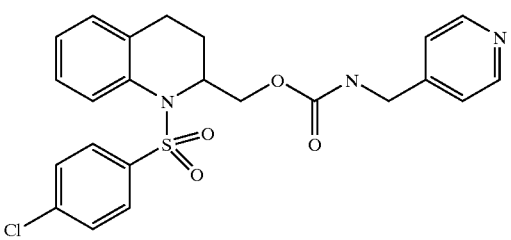 | 473(M + 1)+ |
| 48 | 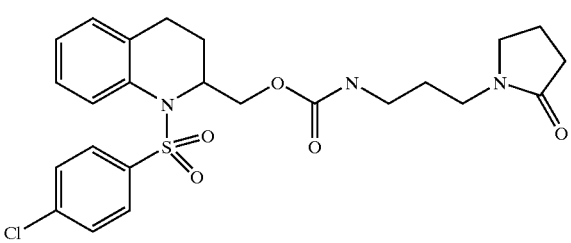 | 507(M + 1)+ |
| 49 | 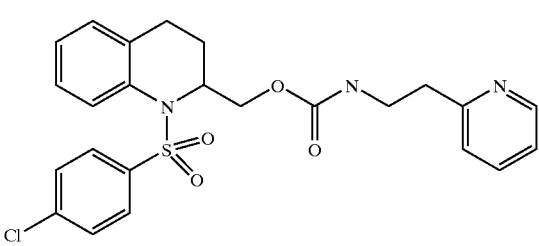 | 487(M + 1)+ |

TABLE 1-continued
| Ex. | Structure | LC-MS (ESI) m/e |
|---|---|---|
| 50 | 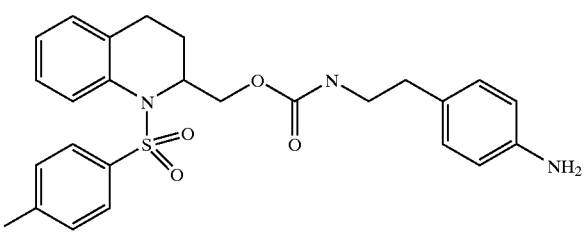 | 501(M + 1)+ |
| 51 | 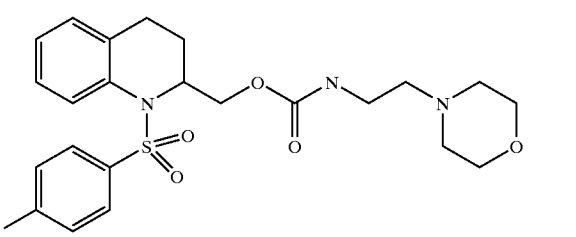 | 495(M + 1)+ |
| 52 | 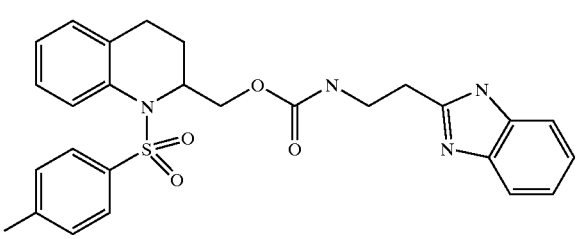 | 526(M + 1)+ |
| 53 | 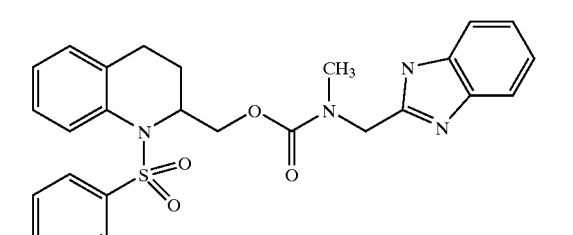 | 526(M + 1)+ |
| 54 | 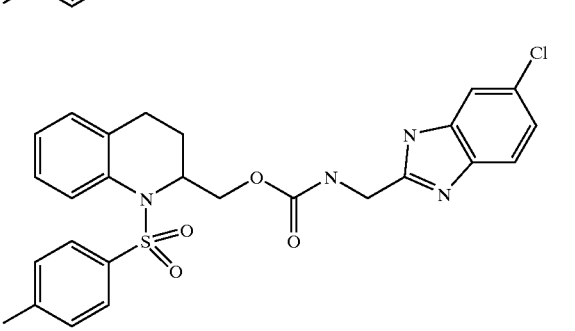 | 546(M + 1)+ |
| 55 | 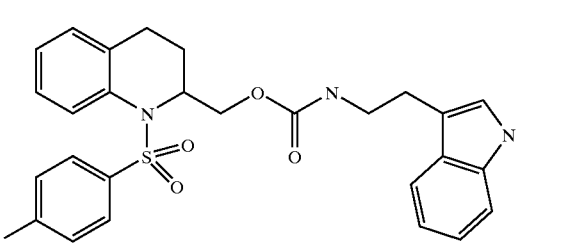 | 525(M + 1)+ |

TABLE 1-continued

| Ex. | Structure | LC-MS (ESI) m/e |
|---|---|---|
| 56 | 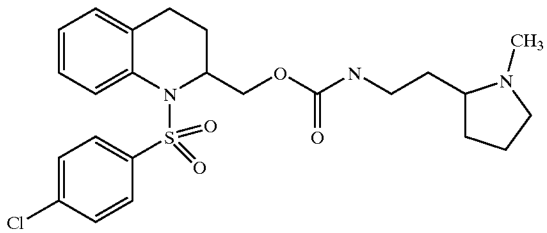 | 493(M + 1)+ |
| 57 | 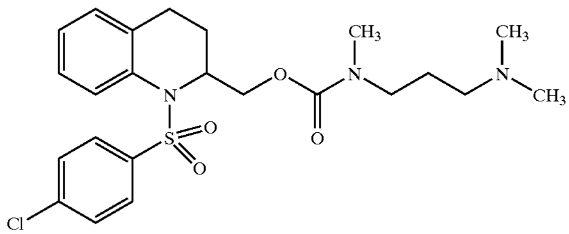 | 481(M + 1)+ |
| 58 | 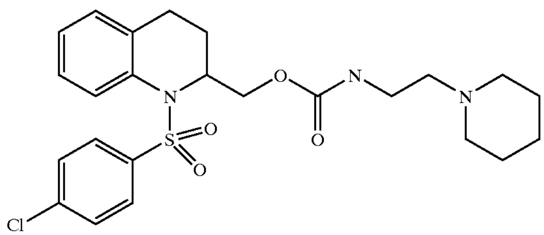 | 493(M + 1)+ |
| 59 | 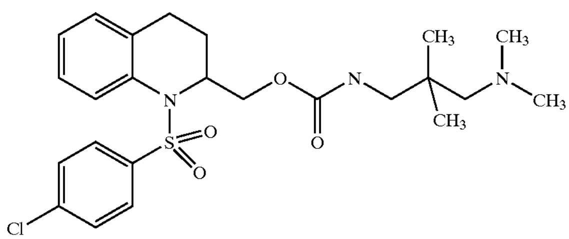 | 495(M + 1)+ |
| 60 | 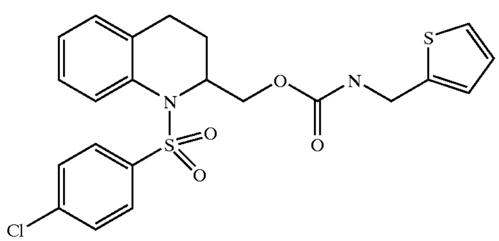 | 478(M + 1)+ |
| 61 | 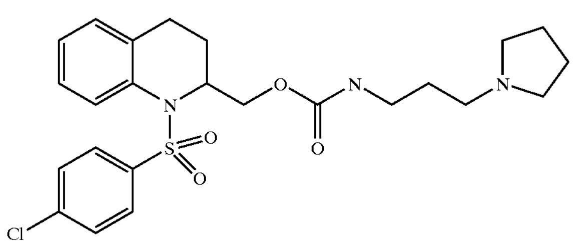 | 493(M + 1)+ |

TABLE 1-continued
| Ex. | Structure | LC-MS (ESI) m/e |
|---|---|---|
| 62 | 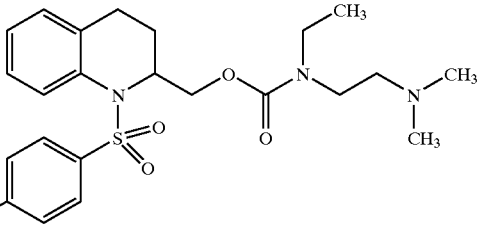 | 481(M + 1)+ |
| 63 | 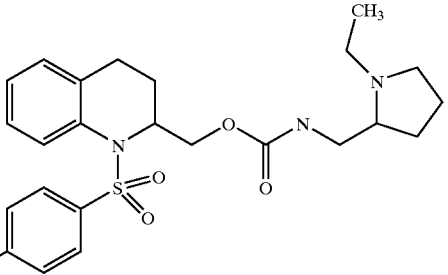 | 493(M + 1)+ |
| 64 | 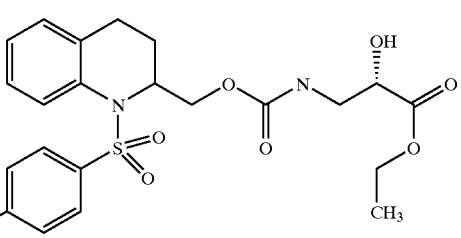 | 497(M + 1)+ |
| 65 | 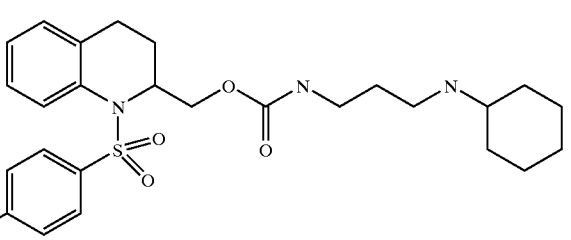 | 520(M+), 320 |
| 66 | 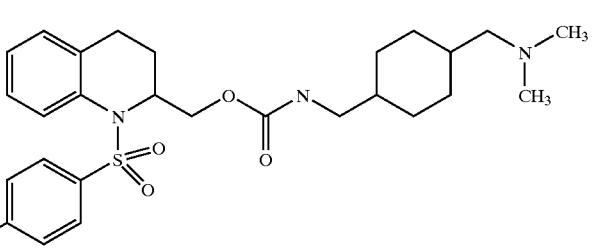 | 534(M+) |
| 67 | 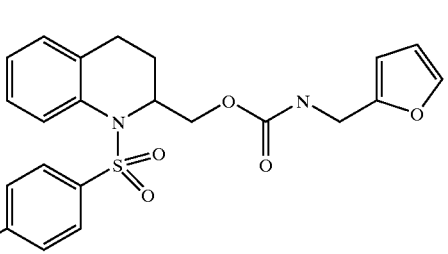 | 461(M+), 320, 286 |

TABLE 1-continued

| Ex. | Structure | LC-MS (ESI) m/e |
|---|---|---|
| 68 | 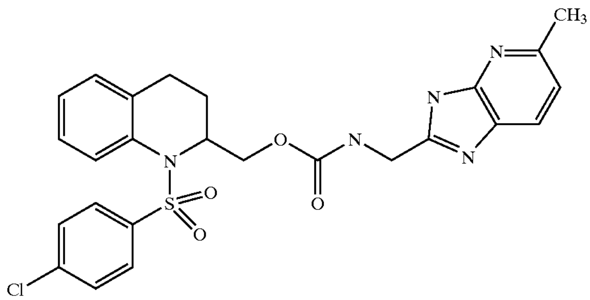 | 526(M+) |
| 69 | 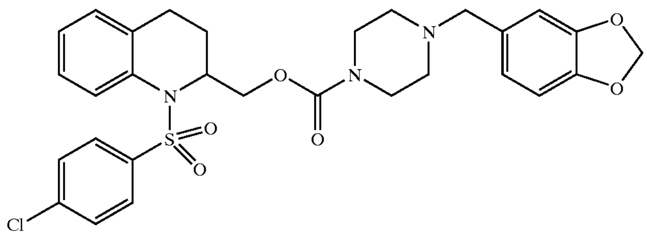 | 584(M+) |
| 70 | 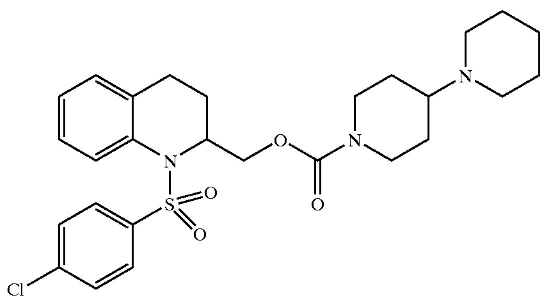 | 532(M+) |
| 70A | ENANTIOMER 1 | 532 (M+) |
| 71 | 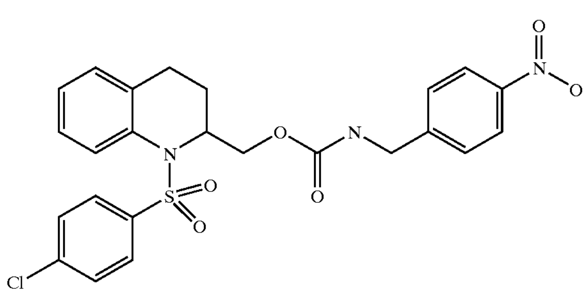 | 516(M+), 341, 320 |

TABLE 1-continued
| Ex. | Structure | LC-MS (ESI) m/e |
|---|---|---|
| 72 | 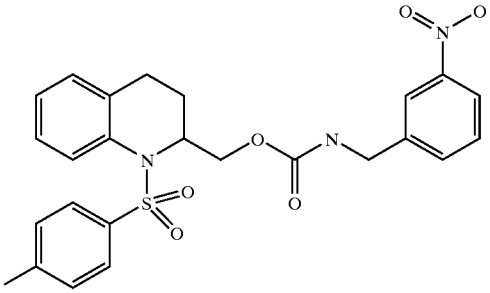 | 516(M+), 341, 320 |
| 73 | 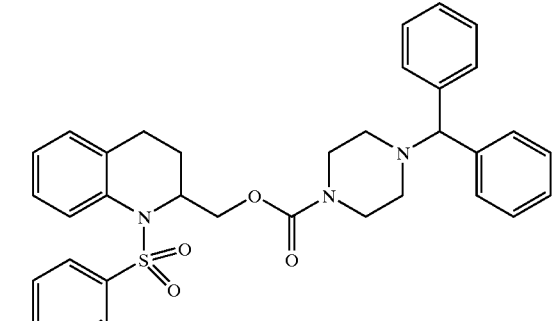 | 616(M+) |
| 74 | 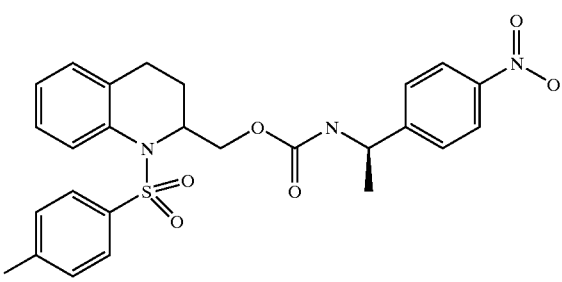 | 530(M+), 355 338, 320 |
| 75 | 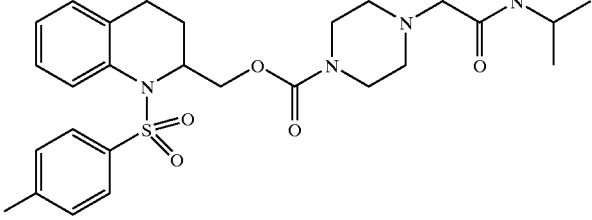 | 549(M+) |
| 76 | 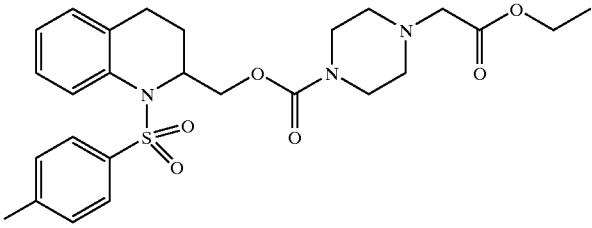 | 536(M+) |

TABLE 1-continued

| Ex. | Structure | LC-MS (ESI) m/e |
|---|---|---|
| 77 | 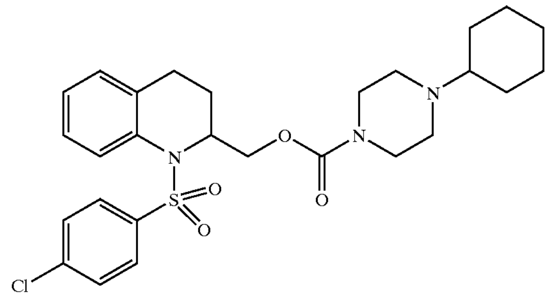 | 532(M+) |
| 78 | 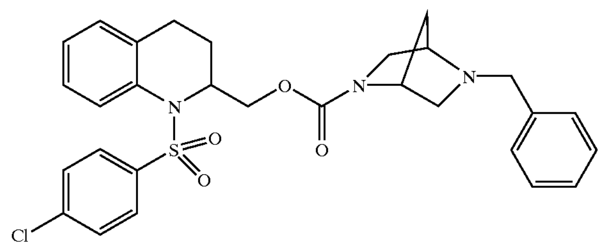 | 552(M+) |
| 79 | 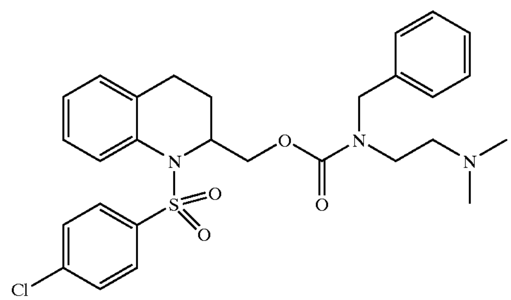 | 547(M+), 320 |

EXAMPLE 81

Synthesis of Pyridin-2-ylmethyl-carbamic Acid 1-(4-chloro-benzenesulfonyl)-1,2,3,4-tetrahydro-quinolin-3-yl Ester Step 1:

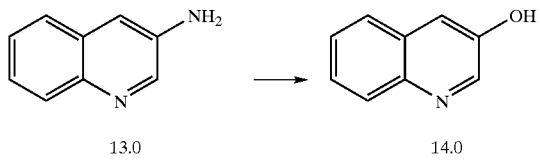

13.0 → 14.0

A mixture containing 3-aminoquinoline 13.0 (10.0 g, 69.4 mmol) and sodium bisulfite (40.0 g, 0.38 mol) in water (100 mL) was heated at reflux for 3 days. The reaction mixture was cooled to room temperature, made basic with 30% NaOH to pH 8 and refluxed for 1 h. After cooling to room temperature, the mixture was filtered to give brown solid. Silica gel chromatography (ethyl acetate:hexane, 50%) of the crude product afforded the title compound (6.7 g, yield 67%) as a solid: $^1$H NMR (300 MHz, CDCl$_3$) δ 10.3 (br s, 1H), 8.54 (m, 1H), 7.84–7.88 (m, 1H), 7.74–7.77 (m, 1H), 7.45–7.48 (m, 3H).

Step 2:

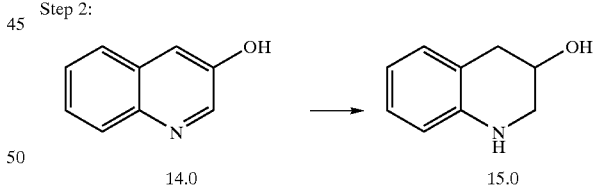

14.0 → 15.0

To a refluxing mixture of 3-hydroxyquinoline 14.0 (2.7 g, 18.6 mmol) in ethanol (60 mL) was added sodium pieces portionwise over a 1 h period. After sodium addition was completed, continued to reflux for 30 min. After cooling the reaction mixture to room temperature, ethanol was removed at reduced pressure, the residue diluted with water, and extracted with ether. The ether phase was dried over magnesium sulfate, filtered and evaporated at reduce pressure to give the title compound (1.5 g, yield 54%): $^1$H NMR (300 MHz, CDCl$_3$) δ 6.77–6.82 (m, 2H), 6.35–6.39 (m, 2H), 5.53 (s, 1H), 4.82 (br s, 1H), 3.82–3.87 (m, 1H), 3.14–3.20 (m, 1H), 2.74–2.88 (m, 2H), 2.47–2.54 (m, 1H).

Step 3:

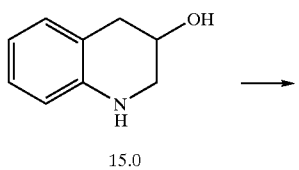
15.0

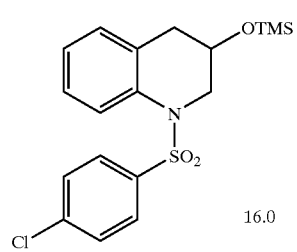
16.0

To a solution of 3-(hydroxy)tetrahydroquinoline 15.0 (1.3 g, 8.72 mmol) in dichloroethane (20 mL) containing triethylamine (2. mL, 14.35 mmol) was added trimethylsilyl chloride (1.2 mL, 9.45 mmol) at 0° C. The mixture was stirred for 30 min at 0° C. followed by addition of triethylamine (2.0 mL) and p-chlorobenzenesulfonyl chloride (1.96 g, 9.29 mmol). The mixture was stirred at reflux for 16 h, and water was added. The organic layer was separated, washed with water, dried over magnesium sulfate, and concentrated. Silica gel chromatography (ethyl acetate:hexane 3%) of the concentrate gave the title compound (1.55 g, yield 45%) as pale yellow oil: $^1$H NMR (300 MHz, CDCl$_3$)δ 6.98–7.74 (m, 8H), 4.05–4.13 (m, 1H), 3.74–3.88 (m, 1H), 3.32–3.41 (dd, 1H, J=7.5, 7.5 Hz), 2.72–2.81 (dd, 1H, J=8.25, 8.25 Hz), 2.36–2.47 (dd, 1H, J=7.5, 7.5 Hz), 1.46–1.60 (m, 1H), 0.11 (s, 9H).

Step 4:

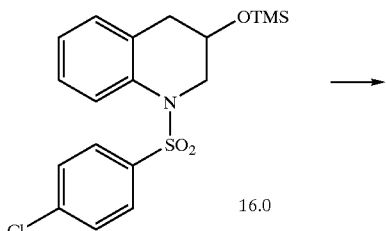
16.0

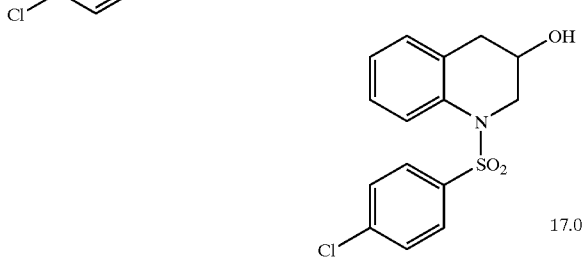
17.0

To a solution of 16.0 (1.5 g, 3.8 mmol) in anhydrous methanol (12 mL) was added solid potassium carbonate (4 mg, 0.03 mmol). The mixture was stirred for 45 min at 0° C., and then acidified with glacial acetic acid. The mixture was extracted with ethyl acetate, dried over magnesium sulfate, and concentrated to give the title compound (1.2 g, yield 98%) as a yellow viscous oil, which was used as is in the next reaction: LC-MS (ESI) m/e 324 (M+1)$^+$.

Step 5:

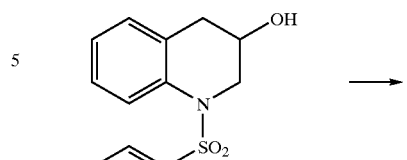
17.0

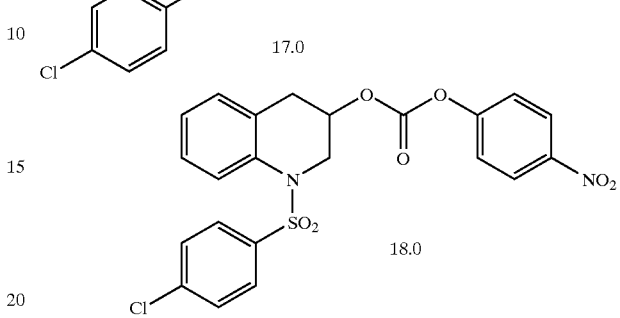
18.0

To a solution of 17.0 (1.20 g, 3.72 mmol) in THF (17 mL) and acetonitrile (3 mL) was added pyridine (255 mg, 3.21 mmol) followed by 4-nitrophenyl chloroformate (820 mg, 4.06 mmol). The resulting mixture was allowed to stir at 22° C. for 16 h. The solvents were removed at reduced pressure, and the product was dissolved in ether. The ether phase was washed with water, brine, dried over magnesium sulfate, and concentrated. Silica gel chromatography (ethyl acetate:hexane, 15%) of the concentrate gave the title compound (1.2 g, yield 66%) as crystalline solid, m.p.=106–110° C.: $^1$H NMR (300 MHz, CDCl$_3$)δ 8.27–8.32 (m, 2H), 7.67–7.12 (m, 3H), 7.36–7.44 (m, 3H), 7.09–7.28 (m, 4H), 5.02–5.09 (m, 1H), 4.06–4.18 (m, 2H), 2.95–3.03 (dd, 1H, J=6.0, 5.7 Hz), 2.78–2.85 (dd, 1H, J=5.4, 5.4 Hz).

Step 6:

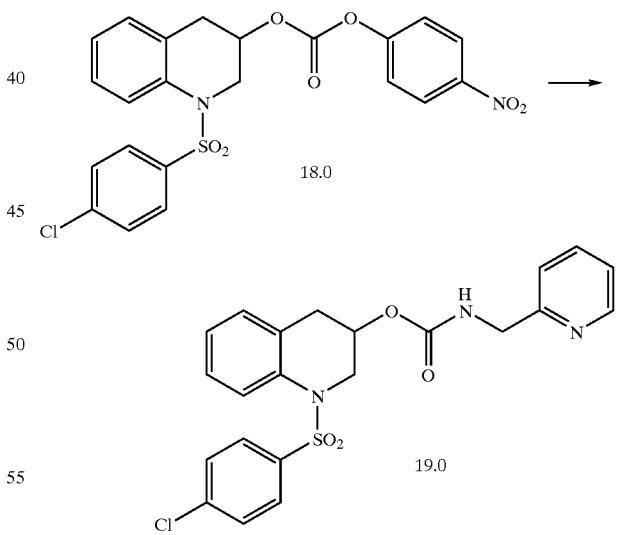

To a solution of the above carbonate 18.0 (50 mg, 0.102 mmol) in methanol (0.5 ml) was added 2-aminomethyl pyridine(55 mg, 0.51 mmol). The resulting mixture was allowed to stir for 16 h at 22° C., then concentrated at reduced pressure. Silica gel chromatography (methanol in CH$_2$Cl$_2$, 5%) of the concentrate afforded the title compound (47 mg, yield Quant.): LC-MS (ESI) m/e 458 (M$^+$), 306.

Following procedures similar to of the of Example 81, the compounds in Table 2 were prepared. In Table 2, "Ex." represents "Example".

TABLE 2

| Ex. | Structure | LC-MS (ESI) m/e |
|---|---|---|
| 82 | 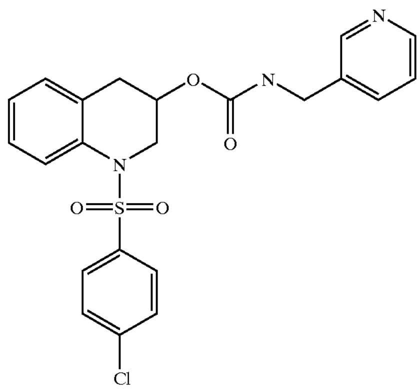 | 458(M+), 306 |
| 83 | 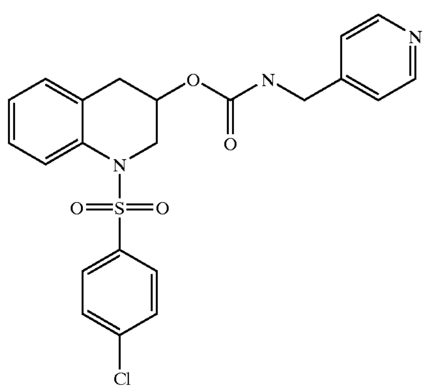 | 458(M+), 306 |
| 84 | 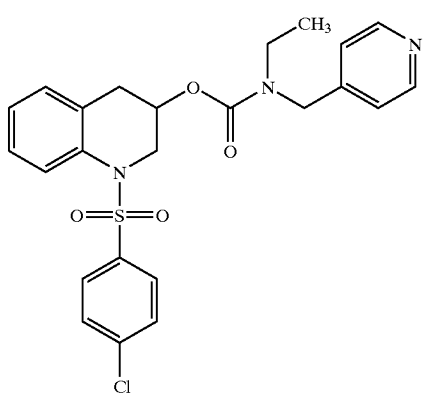 | 486(M+), 306 |
| 85 | 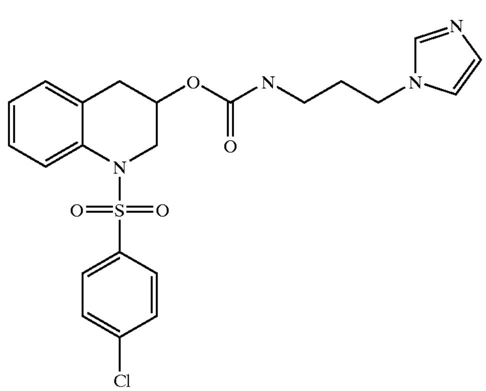 | 475(M+), 306 |

TABLE 2-continued

| Ex. | Structure | LC-MS (ESI) m/e |
|---|---|---|
| 86 | 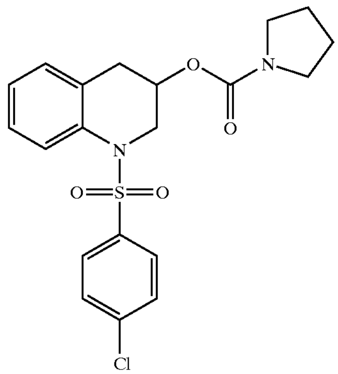 | 421(M+), 306 |
| 87 | 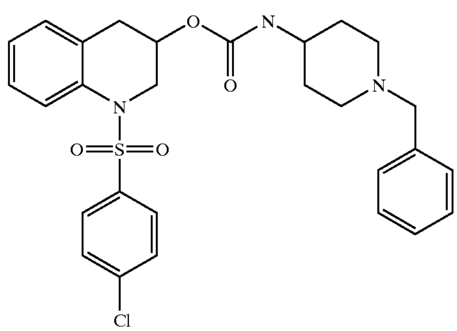 | 540(M+), 306 |
| 88 | 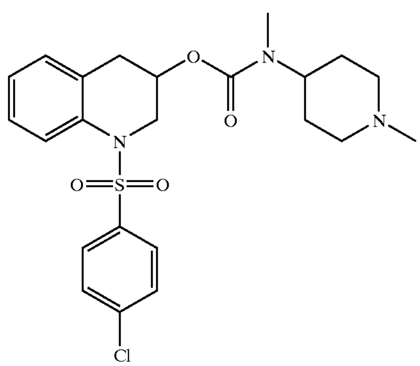 | 478(M+), 306 |
| 89 | 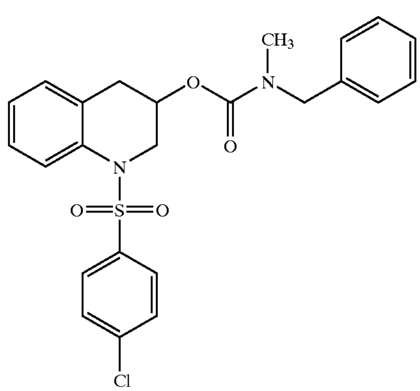 | 473(M+), 306 |

TABLE 2-continued

| Ex. | Structure | LC-MS (ESI) m/e |
|---|---|---|
| 90 | 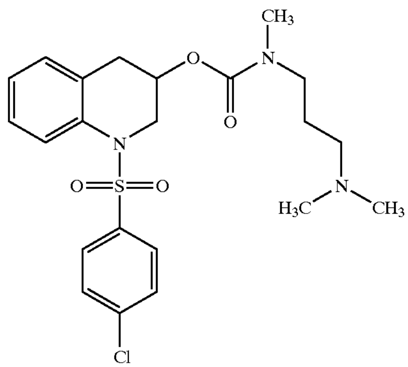 | 466(M+), 306 |
| 91 | 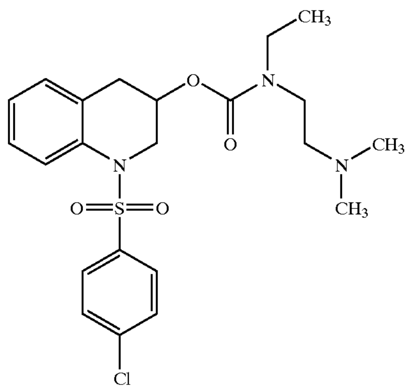 | 466(M+), 306 |

EXAMPLE 93

Synthesis of 1-(4-Chloro-benzenesulfonyl)-2-(4-thiomorpholin-4-ylmethyl-phenyl)-1,2,3,4-tetrahydro-quinoline Step 1:

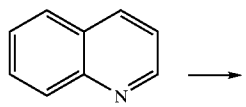

20.0

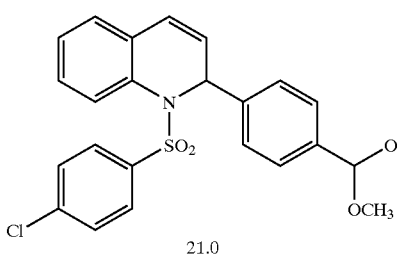

21.0

To a solution of 4-bromobenzaldehyde dimethylacetal (6.1 g, 26.3 mmol) in THF (100 mL) maintained at −78° C. was slowly added nBuLi (12.8 mL, 25.6 mmol, 2M in THF). The resulting yellow solution was stirred for 1 h at −78° C., then a solution of quinoline (3.39 g, 26.2 mmol) in THF (20 mL) was slowly added. The resulting pale brown solution was stirred for 30 min at −78° C. and additional 30 min at 0° C. The mixture was cooled to −78° C. and a solution of p-chlorobenzenesulfonyl fluoride (5.0 g, 25.6 mmol) in THF (30 mL) was slowly added. The mixture was stirred for 1 h at −78° C. and at ambient temperature for 16 h. Quenched with water, removed the bulk of the THF under reduced pressure, and the aqueous residue was extracted with ethyl acetate. The organic phase was dried over magnesium sulfate, and concentrated to yellow oil. Trituration with 10% ethyl acetate:hexane gave white crystals. Filtered, washed crystals with 10% ethyl acetate:hexane to afford the title compound (7.96 g, yield 66%); m.p.=134–136° C.; MSFAB m/e 455 (base), 424, 280, 248.

Step 2:

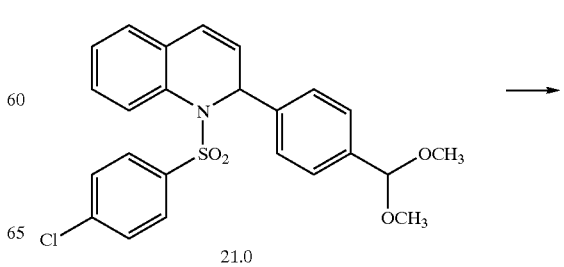

21.0

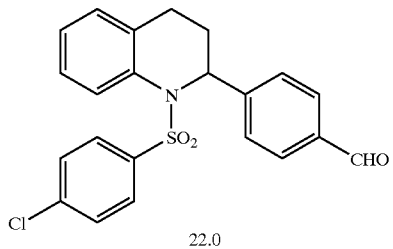

22.0

A solution containing 21.0 (5.23 g, 11.5 mmol), 5% Rh in carbon (700 mg) in ethyl acetate (100 mL) was hydrogenated at 1 atmosphere and ambient temperature for 2 days. The reaction mixture was filtered through a bed of Celite. The filtrate was concentrated at reduced pressure to give a mixture of reduced starting acetal and the desired product. Silica gel chromatography with ethyl acetate afforded the title compound (1.04 g, yield 21%) as white crystalline solid; m.p.=157–159° C.

Step 3:

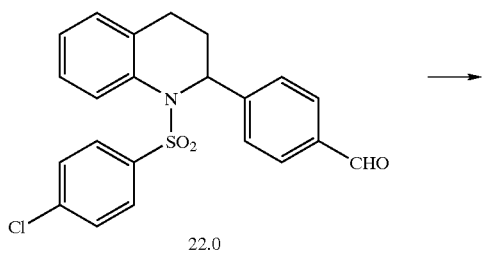

22.0 →

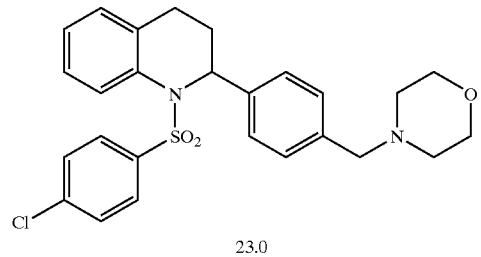

23.0

To a solution of aldehyde 22.0 (50 mg, 0.12 mmol) in dichloroethane (2 mL) was added morpholine (13.1 mg, 0.149 mmol) followed by sodium triacetoxyborohydride (32 mg, 0.15 mmol). The reaction mixture was stirred at ambient temperature for 16 h. The solvent was removed at reduced pressure and the crude product was purified by preparative thin layer chromatography with ethyl acetate to give the title compound (38.6 mg, yield 67%) as white solid; HRFABMS calcd for $C_{26}H_{28}ClN_2O_2S_2$ (MH$^+$): 483.1509. Found 483.1516.

Following procedures similar to those of Example 93, the compounds in Table 3 were prepared. In Table 3, "Ex." represents "Example".

TABLE 3

| Ex. | Structure | HRFABMS |
|---|---|---|
| 94 | 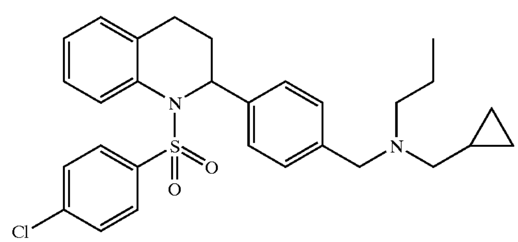 | Calcd for $C_{29}H_{34}ClN_2O_2S$ (MH+) 509.2030<br>Found 509.2023 |
| 95 | 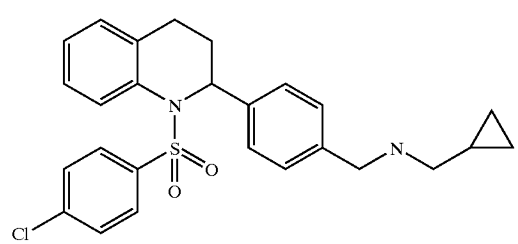 | Calcd for $C_{26}H_{28}ClN_2O_2S_2$ (MH+) 467.1560<br>Found 467.1556 |

TABLE 3-continued

| Ex. | Structure | HRFABMS |
|---|---|---|
| 96 | 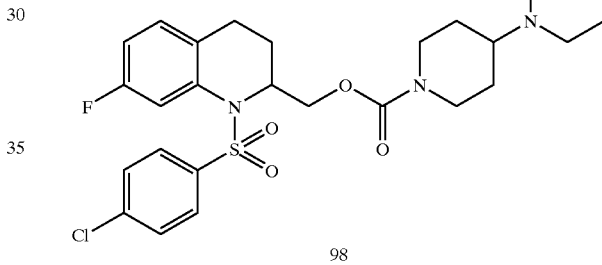 | Calcd for $C_{26}H_{28}ClN_2O_2S_2$ (MH+) 484.1826<br>Found 484.1834 |
| 97 | 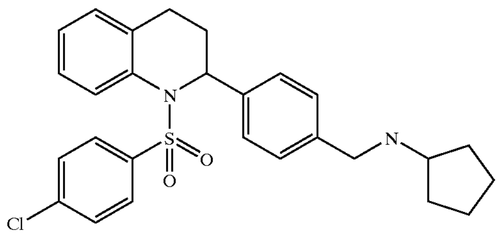 | Calcd for $C_{26}H_{28}ClN_2O_2S_2$ (MH+) 481.1717<br>Found 481.1721 |

EXAMPLE 98

Preparation of Compound of Formula 98

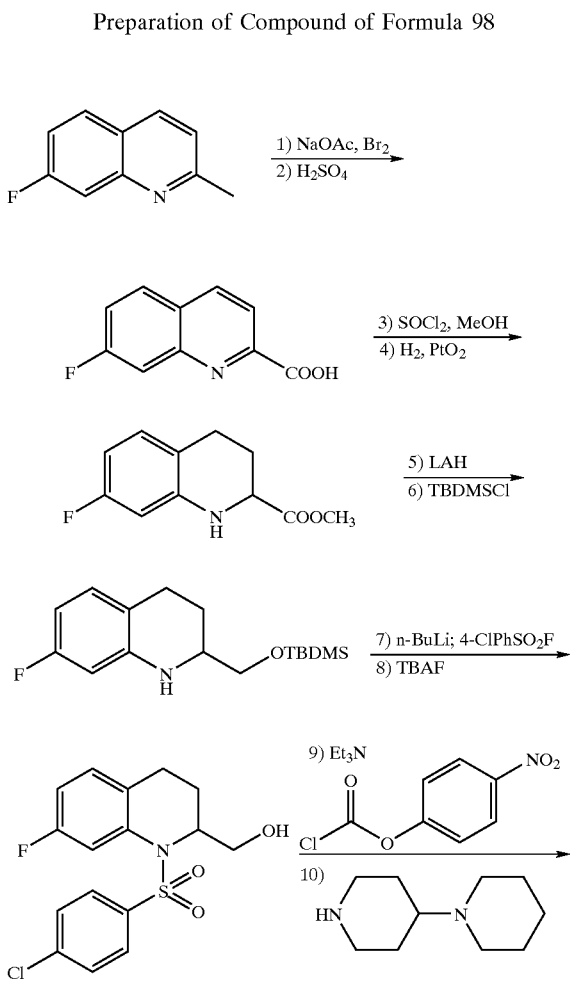

TBDMS = tert-butyldimethylsilyl
TBAF = tetrabutylammonium fluoride

Step 1:

To a solution of 2-methyl-7-fluoroquinoline (26.9 g; 0.17 mol) in acetic acid (180 mL) was added sodium acetate (93 g; 0.68 mol) followed by bromine (26.3 mL; 0.51 mol). The reaction was heated at 90° C. for 1 h then concentrated. The residue was washed with water, dissolved in DCM, dried over $Na_2SO_4$ and concentrated to afford 59.0 g (88%) of an orange solid.

Step 2:

A solution of the product of step 1 (78.8 g; 0.2 mol) and sulfuric acid (600 mL) was heated at 100° C. for 3 days then poured onto ice. The mixture was diluted with ammonium hydroxide until pH>10, the pH was subsequently adjusted to 4 with 85% aqueous phosphoric acid, and the solution was extracted with DCM and EtOAc to provide, after drying over $Na_2SO_4$ and concentration, 30.0 g (79%) of acid.

Step 3:

To a solution of the product of step 2 (30.0 g; 0.16 mol) in anhydrous MeOH (300 mL) was added thionyl chloride (25 mL; 0.32 mol) and the reaction was stirred under reflux for 2 h. After concentration the residue was taken up in 1 N aqueous NaOH and extracted with DCM and EtOAc. The combined organic layers were concentrated then purified by chromatography over silica gel (eluting Hexanes/EtOAc 8:2) to give 11 g (40%) of ester, as an oil.

Step 4:

A solution of the product of step 3 (11.0 g; 54 mmol) and platinum oxide (1.2 g) in anhydrous methanol (100 mL) was hydrogenated at atmospheric pressure for 30 minutes to provide, after filtration over Celite and concentration, 11.7 g (100%) of amino ester, as an oil.

Step 5:

To a solution of the product of step 4 (8.0 g; 38 mmol) in anhydrous THF (150 mL) at −78° C. was added lithium aluminum hydride 1 N in THF (115 mL; 115 mmol) and the reaction was allowed to warm to RT and stirred 2 h. The mixture was quenched with EtOAc, diluted with 1 N NaOH and DCM, filtered over Celite, extracted with DCM, and dried over $Na_2SO_4$. After concentration of the solvents, 6.8 g of amino alcohol (100%) were obtained.

Step 6:

A solution of the product of step 5 (6.8 g; 37.7 mmol), triethylamine (6.3 mL; 45.2 mmol) and tert-butyidimethylsilyl chloride (6.3 g; 41.5 mmol) in DEC (60 mL) was stirred at 60° C. overnight. After concentration, the residue was purified by chromatography over silica gel (eluting Hexanes/EtOAc 9:1) to give 10.6 g (96%) of amine, as an oil.

Step 7:

To a solution of the product of step 6 (10.6 g; 36.0 mmol) in anhydrous THF (100 mL) at −78° C. was added n-butyl lithium 2.5 N in hexanes (15.8 mL; 39.6 mmol) followed slowly by 4-chlorobenzenesulfonyl fluoride (8.4 g; 43.2 mmol) in anhydrous THF (20 mL). The reaction was stirred 30 minutes at −78° C. and allowed to warm to RT overnight. The residue obtained after concentration of the solvents was diluted with DCM and water, extracted with DCM, dried over $Na_2SO_4$ and concentrated. Purification by chromatography over silica gel (eluting Hexanes/EtOAc 95:5 to DCM/EtOAc 95:5) afforded 17.1 g (100%) of O-protected sulfonamide.

Step 8:

A solution of the product of step 7 (17.1 g; 36 mmol) and tetra-n-butylammonium fluoride 1 N in THF (54.6 mL; 54.6 mmol) in anhydrous THF (100 mL) was stirred at room temperature for 2 h. After concentration of the solvent, the residue was diluted with DCM and saturated aqueous sodium bicarbonate, extracted with DCM, dried over $Na_2SO_4$ and concentrated. Purification by chromatography over silica gel (eluting Hexanes/EtOAc 8:2 to 1:1) afforded 9.6 g (75%) of sulfonamide alcohol, as an oil.

Step 9:

To a solution of the product of Step 8 (0.5 g; 1.44 mmol) in anhydrous THF (7 mL) was added para-nitrophenyl chloroformate (0.32 g; 1.55 mmol) followed by triethylamine (0.22 mL; 1.55 mmol) and the reaction was stirred at RT overnight. The mixture was concentrated, dissolved in DCM and washed with ice-cooled 5% aqueous citric acid. After concentration of the solvent, the residue was purified by chromatography over silica gel (eluting Hexanes/EtOAc 8:2 to EtOAc) to give 700 mg (95%) of carbonate, as an oil.

Step 10:

The product of step 9 (40 mg) was converted to the title compound (formula 98) as described in Step 6, Example 1, using 4-piperidinopiperidine at the last stage of the synthesis. After purification by chromatography on silica gel (eluting DCM/EtOAc 7:3), 14.7 mg of product were obtained: $^1$H-NMR (300 mhz, $CDCl_3$)δ7.48 (dd, 1 h), 7.45 (d, 2 h), 7.37 (d, 2 h), 6.96 (m, 1 h), 6.86 (dd, 1 h), 4.59 (br s, 1 h), 3.85–4.30 (m, 4 h), 2.30–2.80 (m, 8 h), 1.20–2.00 (m, 13 h); HRMS ($MH^+$) 550.1935.

EXAMPLE 99

Preparation of the Compound of Formula 99

The compound of formula 99 was prepared similar to the above-described preparation of the compound of formula 98, except that N,N'-dimethyl4-aminopiperidine was used in place of 4-piperidnopiperidine in the last step. LC-MS (ESI), m/e 510 ($M^+$).

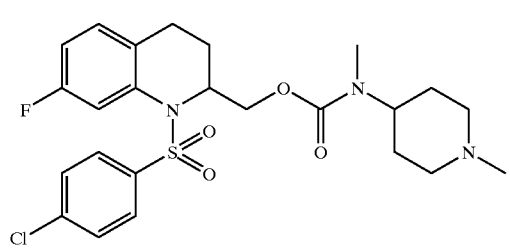

EXAMPLE 100

Preparation of Compound of Formula 100

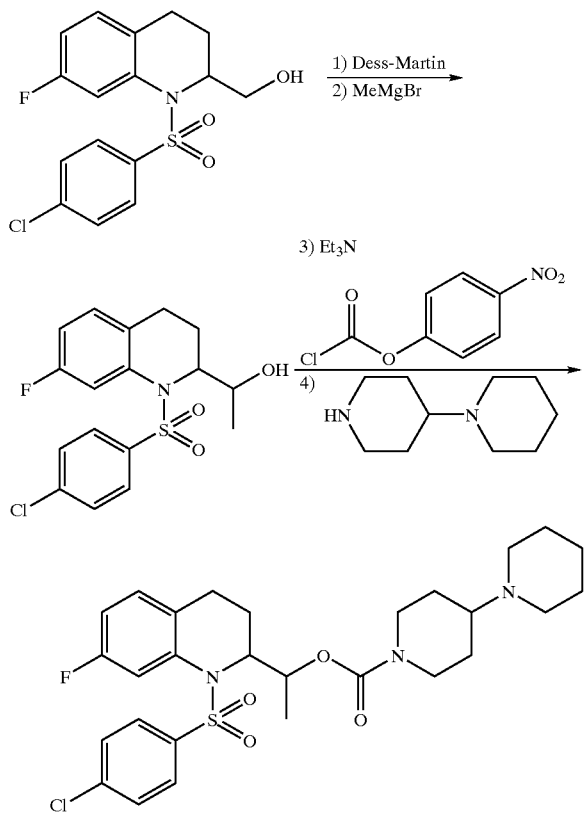

Step 1:

To a solution of the product of Example 98, Step 8 (0.5 g; 1.4 mmol) in DCM (10 ml) was added Dess-Martin periodinane (0.72 g; 1.7 mmol) followed by sodium bicarbonate (150 mg) and two drops of water. The mixture was stirred overnight at room temperature, then quenched with $Et_2O$ (20 mL), saturated $NaHCO_3$ and sodium thiosulfite (2.0 g) for 20 minutes. The reaction was extracted with $Et_2O$, dried over $Na_2SO_4$ and concentrated to provide 411 mg (83%) of aldehyde.

Step 2:

To a solution of aldehyde product of step 1 (411 mg; 1.15 mmol) in anhydrous THF (8 mL) at 0° C. was added methyl magnesium bromide solution 3 N in $Et_2O$ (0.61 mL; 1.84 mmol) and the reaction was allowed to warm to room temperature for 2 h. The mixture was poured into saturated ammonium chloride, extracted with DCM, and dried over $Na_2SO_4$. After concentration of the solvents, the residue was purified by chromatography over silica gel (eluting Hexanes/EtOAc 7:3) to give 286 mg (68%) of alcohol, as an oil, as a ca 2:1 mixture of diastereoisomers.

Step 3:

To a solution of alcohol product of Step 2 (286 mg; 0.77 mmol) in anhydrous THF (3 mL) was added para-nitrophenyl chloroformate (342 mg; 1.7 mmol) followed by triethylamine (0.4 mL; 1.7 mmol) and the reaction was stirred at reflux overnight. The mixture was concentrated, dissolved in DCM and washed with ice-cooled 5% aqueous citric acid. After concentration of the solvent, the residue was purified by chromatography over silica gel (eluting DCM) to give 430 mg (100%) of carbonate, as an oil, as a ca 2:1 mixture of diastereoisomers.

Step 4:

The product of Step 3 (87 mg) was converted to the title compound according to Step 6 of Example 1, using 4-piperidinopiperidine at the last stage of the synthesis. After purification by chromatography on silica gel (eluting Hexanes/isopropyl alcohol 1:1), 13.1 mg of product were obtained, as a ca 2:1 mixture of diastereoisomers: HRMS $(MH^+)$ 564.2091.

Assay:

Gamma secretase activity was determined as described by Zhang et a. (*Biochemistry*, 40 (16), 5049–5055, 2001). Activity is expressed either as a percent inhibition or as the concentration of compound producing 50% inhibition of enzyme activity.

Reagents. Antibodies W02, G2–10, and G2–11 were obtained from Dr. Konrad Beyreuther (University of Heidelberg, Heidelberg, Germany). W02 recognizes residues 5–8 of Aβ peptide, while G2–10 and G2–11 recognize the specific C-terminal structure of Aβ40 and Aβ42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK 167 was from Enzyme Systems Products (Livermore, Calif.).

cDNA Constructs, Tissue Culture, and Cell Line Construction. The construct SPC99-Lon, which contains the first 18 residues and the C-terminal 99 amino acids of APP carrying the London mutation, has been described (Zhang, L., Song, L., and Parker, E. (1999) *J. Biol. Chem.* 274, 8966–8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for A production by inducing C99 expression with 0.1 g/mL tetracycline for 16–20 h and analyzing conditioned media with a sandwich immunoassay (see below). One of the clones, designated as pTRE.15, was used in these studies.

Membrane Preparation. C99 expression in cells was induced with 0.1 g/mL tetracycline for 20 h. The cells were pretreated with 1 M phorbol 12-myristate 13-acetate (PMA) and 1 M brefeldin A (BFA) for 5–6 h at 37 C. before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70 C.

γ-Secretase Reaction and Aβ Analysis. To measure γ-secretase activity, membranes were incubated at 37 C. for 1 h in 50 L of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2–10 and biotin-W02, while Aβ 42 was identified with TAG-G2–11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γsecretase activity described were confirmed using more than five independent membrane preparations.

The compounds of Examples 1 to 100 had an $IC_{50}$ within the range of about 0.030 to about 24.450 μM. The compounds of Examples 35, 39, 41, 43, 56, 58, 59, 61, 70, 70A, 78, 98, 99 and 100 had an $IC_{50}$ within the range of about 0.030 to about 0.535 μM.

Pharmaceutical compositions can comprise one or more of the compounds of formula 1.0. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose.

Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of the invention may also be deliverable subcutaneously.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

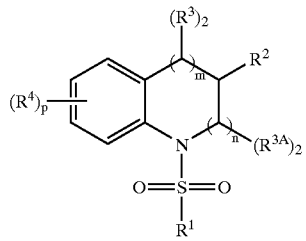

(1.0)

or a pharmaceutically acceptable salt or solvate thereof, wherein:
(A) $R^1$ is selected from:
  (1) unsubstituted aryl;
  (2) aryl substituted with one or more (e.g., 1–3) $R^5$ groups;
  (3) heteroaryl; or
  (4) heteroaryl substituted with one or more (e.g., 1–3) $R^5$ groups;
(B) $R^2$ is selected from:
  (1) alkyl,
  (2) —X(CO)Y;
  (3) —(CR$^3$)$_{1-4}$X(CO)Y; or
  (4) any of the groups for $R^1$,
(C) Each $R^3$ is independently selected from:
  (1) H, or
  (2) alkyl;
(D) Each $R^{3A}$ is independently selected from:
  (1) H; or
  (2) alkyl;
(E) $R^4$ is independently selected from:
  (1) halogen;
  (2) —CF$_3$;
  (3) —OH;
  (4) —Oalkyl;
  (5) —OCF$_3$;
  (6) —CN;
  (7) —NH$_2$;
  (8) —CO$_2$alkyl;
  (9) —CONR$^6$R$^7$;
  (10) -alkylene-NR$^6$R$^7$;
  (11) —NR$^6$COalkyl;
  (12) —NR$^6$COaryl;
  (13) —NR$^6$COheteroaryl; or
  (14) —NR$^6$CONR$^6$R$^7$;
(F) $R^5$ is independently selected from:
  (1) halogen;
  (2) —CF$_3$;
  (3) —OH;
  (4) —Oalkyl;
  (5) —OCF$_3$;
  (6) —CN;
  (7) —NH$_2$;
  (8) —CO$_2$alkyl;
  (9) —CONR$^6$R$^7$;
  (10) alkylene-NR$^6$R$^7$;
  (11) —NR$^6$COalkyl;
  (12) —NR$^6$COaryl;
  (13) —NR$^6$COheteroaryl;
  (14) —NR$^6$CONR$^6$R$^7$;

(G) X is selected from:
  (1) —O—;
  (2) —NH;
  (3) —N-alkyl; or
(H) Y is selected from:
  (1) —NR$^6$R$^7$; or
  (2) —N(R$^3$)(CH$_2$)$_{2-6}$NR$^6$R$^7$;
(I) R$^6$ and R$^7$ are independently selected from:
  (1) H;
  (2) alkyl;
  (3) cycloalkyl,
  (4) -arylalkyl;
  (5) -heteroarylalkyl;
  (6)

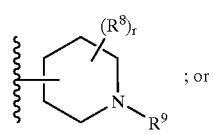
; or (7)

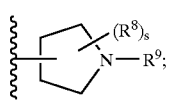
;

(J) R$^6$ and R$^7$ taken together with the nitrogen atom to which they are bound form a heterocycloalkyl group selected from:

(c) 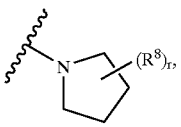

(d) 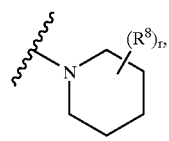

(e) 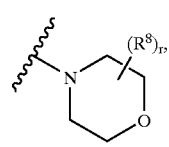

(f) 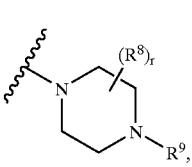

(g) 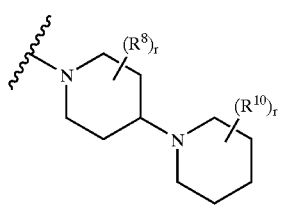 or (h) 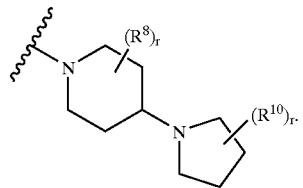

(K) Each R$^8$ is independently selected from: (1) alkyl; or (2) alkyl substituted with 1 to 4 hydroxy groups;
(L) Each R$^9$ is independently selected from:
  (1) H;
  (2) alkyl;
  (3) alkyl substituted with 1 to 4 hydroxy groups;
  (4) cycloalkyl;
  (5) cycloalkyl substituted with 1 to 4 hydroxy groups;
  (6) -arylalkyl;
  (7) -heteroarylalkyl;
  (8) —COOalkyl; or
  (9) any of the groups for R$^1$;
(M) Each R$^{10}$ is independently selected from:
  (1) H; or
  (2) alkyl;
(N) m is 0 to 3, and n is 0 to 3, such that m+n is 1, 2, 3 or 4;
(O) p is 0 to 4;
(P) r is 0 to 4;
(Q) s is 0 to 3; and
(R) with the proviso that compounds of formula 1.0 do not include:

(1.0A)
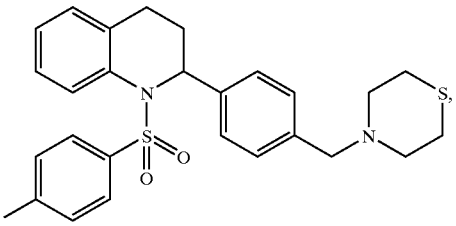

(1.0B)
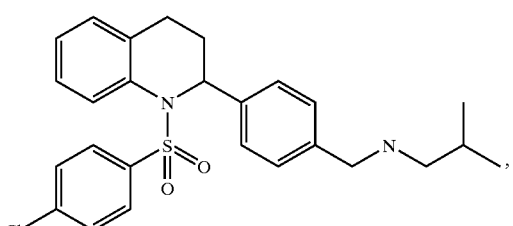

(1.0C)
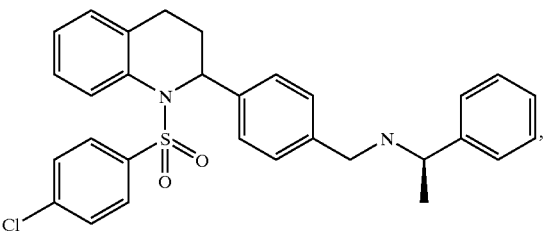

-continued

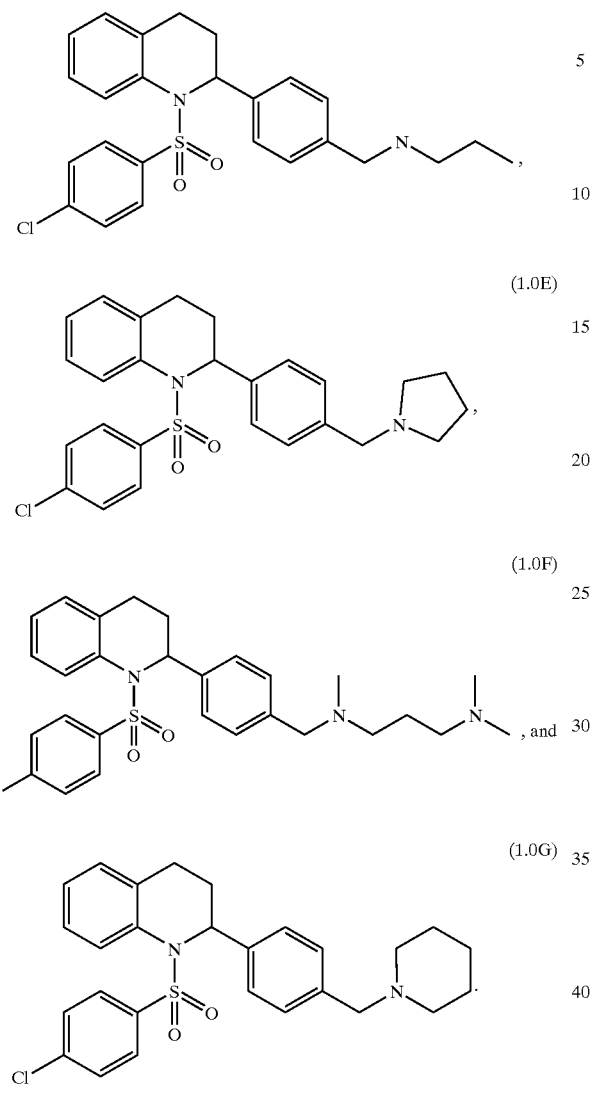

(S) and with the further proviso that when n=0 and m=2, $R^2$ is not alkyl, dialkyl or alkenyl.

2. The compound of claim 1 wherein:
  (A) $R^1$ is aryl substituted with one or more $R^5$ groups;
  (B) n is 0 or 1 and m is 1 or 2 such that m+n is 2;
  (C) p is 0 or 1, and when p is 1 $R^4$ is halo; and
  (D) $R^2$ is —X(CO)Y or —$(CR^3{}_2)_{1-4}$X(CO)Y.

3. The compound of claim 2 wherein:
  (A) $R^1$ is phenyl substituted with one or more $R^5$ groups; and
  (B) n is 0 and m is 2.

4. The compound of claim 3 wherein $R^1$ is phenyl substituted with one or more halo atoms.

5. The compound of claim 1 wherein:
  (A) $R^1$ is aryl substituted with one or more $R^5$ groups;
  (B) n is 0 or 1 and m is 1 or 2 such that m+n is 2;
  (C) p is 0 or 1, and when p is 1 $R^4$ is halo;
  (D) $R^2$ is —X(CO)Y or —$(Cr^3{}_2)_{1-4}$X(CO)Y;
  (E) X is O;
  (F) Y is —$NR^6R^7$; and (G) $R^6$ and $R^7$ are independently selected from: H, methyl, ethyl —$(C_3$–$C_8)$cycloalkyl, -aryl$(C_1$–$C_6)$alkyl, 4-pyridylmethyl,

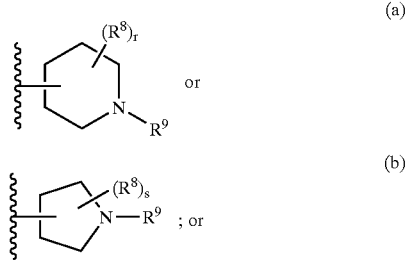

(H) $R^6$ and $R^7$ taken together with the nitrogen atom to which they are bound form a heterocycloalkyl group selected from:

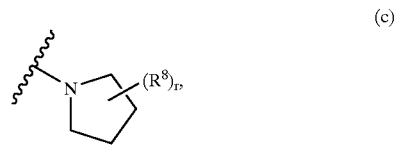

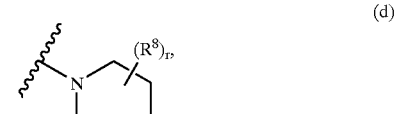

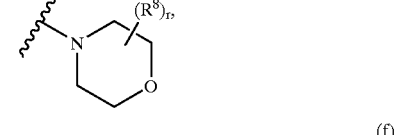

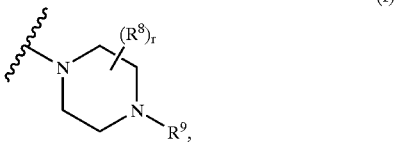

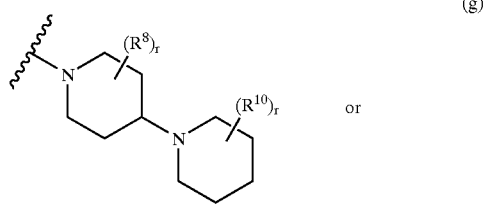

6. The compound of claim 5 wherein:
  (A) $R^1$ is phenyl substituted with one or more $R^5$ groups;
  (B) n is 0 and m is 2 such that m+n is 2;

(C) said group

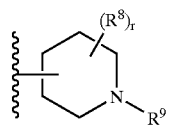

is a group of the formula:

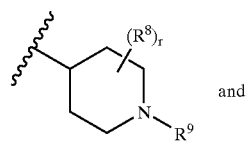

and (D) said group

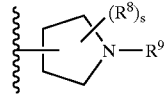

is a group of the formula:

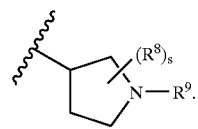

7. The compound of claim 6 wherein $R^1$ is phenyl substituted with one or more halo atoms.

8. The compound of claim 1 selected from a final compound of Examples 1 to 100.

9. The compound of claim 1 selected from a final compound of Examples 35, 39, 41, 43, 56, 58, 59, 61, 70, 70A, 77, 78, 98, 99 or 100.

10. A pharmaceutical composition comprising at least one compound of claim 1 and at least one pharmaceutically acceptable carrier.

11. A pharmaceutical composition comprising at least one compound of claim 9 and at least one pharmaceutically acceptable carrier.

12. A method of inhibiting gamma-secretase in a patient in need of such treatment comprising administering to said patient an effective amount of a compound of claim 1.

13. A method of treating neurodegenerative diseases in a patient in need of such treatment comprising administering to said patient an effective amount of a compound of claim 1.

14. A method of inhibiting the deposition of beta amyloid protein in a patient in need of such treatment comprising administering to said patient an effective amount of a compound of claim 1.

15. A method of treating Alzheimer's disease in a patient in need of such treatment comprising administering to said patient an effective amount of a compound of claim 1.

* * * * *

UNITED STATES PATENT AND TRADEMARK OFFICE
CERTIFICATE OF CORRECTION

PATENT NO. : 6,683,091 B2
DATED : January 27, 2004
INVENTOR(S) : T. Asberom et al.

It is certified that error appears in the above-identified patent and that said Letters Patent is hereby corrected as shown below:

<u>Title page,</u>
Item [75], Inventors, "Theodoros Asberom" should read -- Theodros Asberom --

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,683,091 B2
DATED        : January 27, 2004
INVENTOR(S)  : T. Asberom et al.

It is certified that error appears in the above-identified patent and that said Letters Patent is hereby corrected as shown below:

Column 66,
Lines 27 and 28, replace the phrase "m is 0 to 3, and n is 0 to 3, such that m+n is 1,2,3, or 4" with -- m is 2, and n is 0 --;

Column 67,
Lines 46 and 47, delete lines beginning with "(S)" and ending with "alkenyl".
Lines 50 and 62, delete lines beginning with "(B)" and ending with "2;";
Line 51, replace "(C) with -- (B) --;
Line 52, add -- (C) -- before "$R^2$";
Line 55, delete "(A)";
Lines 56 and 57, delete lines beginning with "and"and ending with "2";
Line 63, replace "(C)"with -- (B) --;
Line 64, replace "(D)" with -- (C) --;
Line 65, replace "(E)" with -- (D) --;
Line 66, replace "(F)" with -- (E) --;

Column 68,
Line 1, replace "(G)" with -- (F) --;
Line 18, replace "(H)" with -- (G) --;
Line 66, delete line, beginning with "(B)" and ending with "2;";

Column 69,
Line 1, replace "(C) " with -- (B) --;
Line 26, replace "(D)" with -- (C) --.

Signed and Sealed this

Twenty-fifth Day of January, 2005

JON W. DUDAS
*Director of the United States Patent and Trademark Office*